(12) United States Patent
Sethi et al.

(10) Patent No.: US 9,688,713 B2
(45) Date of Patent: *Jun. 27, 2017

(54) GALACTOSIDE INHIBITOR OF GALECTINS

(71) Applicant: GALECTO BIOTECH AB, Copenhagen (DK)

(72) Inventors: Tariq Sethi, Haddington (GB); Alison Mackinnon, Edinburgh (GB); Hakon Leffler, Lund (SE); Ulf Nilsson, Lund (SE)

(73) Assignee: Galecto Biotech AB, Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/966,427

(22) Filed: Dec. 11, 2015

(65) Prior Publication Data

US 2016/0096861 A1    Apr. 7, 2016

Related U.S. Application Data

(63) Continuation of application No. 13/832,672, filed on Mar. 15, 2013, now Pat. No. 9,243,021.

(60) Provisional application No. 61/728,491, filed on Nov. 20, 2012, provisional application No. 61/727,272, filed on Nov. 16, 2012, provisional application No. 61/720,641, filed on Oct. 31, 2012.

(51) Int. Cl.

| | | |
|---|---|---|
| *C07H 19/056* | (2006.01) | |
| *C07H 3/04* | (2006.01) | |
| *G01N 33/68* | (2006.01) | |
| *A61K 9/00* | (2006.01) | |
| *A61K 31/7008* | (2006.01) | |
| *C07H 5/10* | (2006.01) | |
| *A61M 15/00* | (2006.01) | |

(52) U.S. Cl.
CPC ......... *C07H 19/056* (2013.01); *A61K 9/0075* (2013.01); *A61K 9/0078* (2013.01); *A61K 31/7008* (2013.01); *C07H 3/04* (2013.01); *C07H 5/10* (2013.01); *G01N 33/6893* (2013.01); *A61M 15/0085* (2013.01); *A61M 2202/064* (2013.01); *C07B 2200/13* (2013.01); *G01N 2333/4724* (2013.01); *G01N 2800/122* (2013.01)

(58) Field of Classification Search
None
See application file for complete search history.

(56) References Cited

U.S. PATENT DOCUMENTS

| | | | |
|---|---|---|---|
| 7,230,096 B2 | 6/2007 | Nilsson | |
| 7,638,623 B2 | 12/2009 | Nilsson | |
| 7,700,763 B2 | 4/2010 | Leffler | |
| 8,697,862 B2 | 4/2014 | Nilsson | |
| 8,703,720 B2 | 4/2014 | Leffler | |
| 9,243,021 B2 * | 1/2016 | Sethi | G01N 33/6893 |
| 2011/0130553 A1 | 6/2011 | Nilsson | |
| 2012/0165277 A1 | 6/2012 | Leffler | |
| 2014/0011765 A1 | 1/2014 | Nilsson | |
| 2014/0171630 A1 | 6/2014 | Nilsson | |
| 2014/0200190 A1 | 7/2014 | Nilsson | |

FOREIGN PATENT DOCUMENTS

| | | |
|---|---|---|
| WO | 2005113568 | 12/2005 |
| WO | 2005113569 | 12/2005 |
| WO | 2010126435 | 11/2010 |
| WO | 2013110704 | 8/2013 |
| WO | 2014067986 | 5/2014 |

OTHER PUBLICATIONS

MacKinnon et al., American Journal of Respiratory and Critical Care Medicine, vol. 185(5), pp. 537-546, Mar. 1, 2012.*
Tejler et al (2005). "Synthesis of O-galactosyl aldoximes as potent LacNAc-mimetic galectin-3 inhibitors". Bioorganic and Medicinal Chemistry Letters 15:2343-2345.
Thijssen et al (2006). "Galectin-1 is essential in tumor angiogenesis and is a target for antiangiogenesis therapy". PNAS 103:15975-15980.
Thijssen et al. (2007). "Galectins in the tumor endothelium: opportunities for combined cancer therapy". Blood 110: 2819-2827.
Toscano et al. (2007). Differential glycosylation of TH1, TH2 and TH-17 effector cells selectively regulates susceptibility to cell death. Nat Immunol 8: 825-834.

(Continued)

*Primary Examiner* — Traviss C McIntosh, III
(74) *Attorney, Agent, or Firm* — Cheryl H. Agris; Agris & von Natzmer, LLP

(57) ABSTRACT

Provided is a compound of the general formula (I):

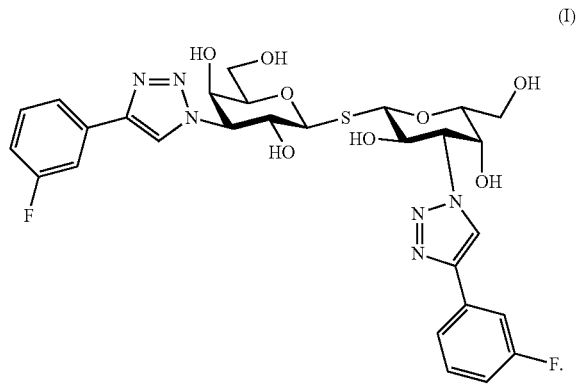

The compound of formula (I) is suitable for treating pulmonary fibrosis, such as Idiopathic pulmonary fibrosis in a mammal. Also provided is a method for treatment of pulmonary fibrosis, such as Idiopathic pulmonary fibrosis in a human subject having a galectin-3 level indicative of pulmonary fibrosis or exacerbation of symptoms as well as a method for making said compound.

7 Claims, 1 Drawing Sheet

(56) References Cited

OTHER PUBLICATIONS

Van Hattum et al (2013). "Tuning the Preference of Thiodigalactoside- and Lactosamine-Based Ligands to Galectin-3 over Galectin-1". J. Med. Chem. 56: 1350-1354.
Van Scherpenzeel et al (2009). "Synthesis and Evaluation of New Thiodigalactoside-Based Chemical Probes to Label Galectin-3". ChemBioChem 10: 1724-1733.
Volarevic et al (2012). "Galectin-3 Deficiency Prevents Concanavalin A-Induced Hepatitis in Mice". Hepatology 55:1954-1964.
Voss et al (2012). "Inhibition of Cell-Free Splicing by Saccharides That Bind Galectins and SR Proteins". Journal of Carbohydrate Chemistry 31: 519-534.
Vrasidas et al (2003). "Rigidified multivalent lactose molecules and their interactions with mammalian galectins: a route to selective inhibitors". Org. Biomol. Chem. 1:803-810.
Wang et al (2013). "Design and synthesis of glycoprotein-based multivalent glyco-ligands for influenza hemagglutinin and human galectin-3". Bioorganic & Medicinal Chemistry 21:2037-2044.
Yang et al (2012). "Synthesis of multivalent N-acetyl lactosamine modified quantum dots for the study of carbohydrate and galectin-3 interactions". Tetrahedron 68:7148-7154.
Zou et al (2005). "Peptides specific to the galectin-3 carbohydrate recognition domain inhibit metastasis-associated cancer cell adhesion". Carcinogensis 26(2):309-318.
Response to EP search report for EP appln. No. 13785446.9 (EP appln. counterpart to U.S. Appl. No. 14/438,977) dated Nov. 25, 2015.
Response to CA Office Action for CA appln. No. 2,794,066 (CA appln. counterpart to U.S. Appl. No. 14/438,977) dated Nov. 23, 2015.
International Preliminary Report on Patentability (IPRP) for PCT/EP2013/072691 (PCT appln. counterpart to U.S. Appl. No. 14/438,977) dated Jan. 26, 2015.
US Notice of Allowance dated Feb. 1, 2016 for U.S. Appl. No. 14/364,169.
US Notice of Allowance dated Sep. 14, 2015 for U.S. Appl. No. 13/832,672.
Decision to Grant Patent for EP13700935.3-1452 (EP counterpart to U.S. Appl. No. 14/364,169), dated Dec. 3, 2015.
US Interview Summary dated Jul. 15, 2015 for U.S. Appl. No. 14/364,169.
US Interview Summary dated Jul. 15, 2015 for U.S. Appl. No. 13/832,672.
US Office Action dated May 21, 2015 for U.S. Appl. No. 13/832,672.
US Office Action dated May 21, 2015 for U.S. Appl. No. 14/364,169.
Applicant's response to Supplemental Search Report EP13700935.3-1452 (EP counterpart to U.S. Appl. No. 14/364,169), dated Feb. 9, 2015.
2nd Written Opinion for PCT/EP2013/072691(PCT counterpart to U.S. Appl. No. 14/438,977) dated Oct. 20, 2014.
Supplemental Search Report EP13700935.3-1452 (EP counterpart to U.S. Appl. No. 14/364,169) dated Sep. 30, 2014.
US Office Action dated Aug. 29, 2014 for U.S. Appl. No. 13/832,672.
International Preliminary Report on Patentability for PCT/EP2013/051339, (PCT counterpart to U.S. Appl. No. 14/364,169 dated Jul. 29, 2014.
Response to 1st Written Opinion for PCT/EP2013/072691 (PCT counterpart to U.S. Appl. No. 14/438,977) dated Jul. 15, 2014.
1st Written Opinion for PCT/EP2013/072691 (PCT counterpart to U.S. Appl. No. 14/438,977) dated Jan. 20, 2014.
Internat'l search report for PCT/2013/072691 (PCT counterpart to U.S. Appl. No. 14/438,977) dated Jan. 2, 2014.
International Search Report and Written Opinion for PCT/EP2013/051339, dated Feb. 28, 2013.

Ingrassia et al (2006). "A Lactosylated Steroid Contributes in Vivo Therapeutic Benefits in Experimental Models of Mouse Lymphoma and Human Glioblastoma". J. Med. Chem. 49: 1800-1807.
John et al. (2003). "Truncated Galectin-3 Inhibits Tumor Growth and Metastasis in Orthotopic Nude Mouse Model of Human Breast". Cancer. Clin. Cancer Res. 9: 2374-2383.
Kahsai et al (2008). "Analogs of Tetrahydroisoquinoline Natural Products That Inhibit Cell Migration and Target Galectin-3 Outside of Its Carbohydrate-binding Site". JBC 283:24534-24545.
Lau et al (2008). "N-Glycans in cancer progression". Glycobiology 18: 750-760.
Lau et al (2007). "Complex N-glycan number and degree of branching cooperate to regulate cell proliferation and differentiation". Cell 129: 123-134.
Leffler et al (2004a). "Introduction to galectins". Glycoconj. J. 19: 433-440.
Leffler, H. Galectins Structure and Function—A Synopsis in Mammalian Carbohydrate Recognition Systems (Crocker, P. ed.) Springer Verlag, Heidelberg, 2001 pp. 57-83.
Leffler et al (1986). "Specificity of binding of three soluble rat lung lectins to substituted and unsubstituted mammalian beta-galactosides". J. Biol. Chem. 261:10119-10126.
Leyden et al (2009). "Synthesis of Bivalent Lactosides Based on Terephthalamide, N, N'-Diglucosylterephthalamide, and Glycophane Scaffolds and Assessment of Their Inhibitory Capacity on Medically Relevant Lectins". J. Org. Chem. 74: 9010-9026.
Lin et al (2009). "Galectin-3 Targeted Therapy with a Small Molecule Inhibitor Activates Apoptosis and Enhances Both Chemosensitivity and Radiosensitivity in Papillary Thyroid Cancer". Mol Cancer Res 7: 1655-1662.
MacKinnon et al (2012). "Regulation of TGF-β1 driven lung fibrosis by Galectin-3". Am. J. Resp. Crit. Care Med. 185: 537-546 (available online Nov. 17, 2011).
MacKinnon et al (2008). "Regulation of alternative macrophage activation by Galectin-3". J. Immun. 180: 2650-2658.
Maljaars et al (2008). "Assessing the inhibitory potency of galectin ligands identified from combinatorial (glyco) peptide libraries using surface plasmon resonance spectroscopy". Analytical Biochemistry 378:190-196.
Massa et al (1993) "L-29, an endogenous lectin, binds to glycoconjugate ligands with positive cooperativity". Biochemistry 32: 260-267.
Moeller et al (2008). "The bleomycin animal model: a useful tool to investigate treatment options for idiopathic pulmonary fibrosis?". Int J Biochem Cell Biol. 40: 362-382.
Moise et al (2011). "Toward Bioinspired Galectin Mimetics: Identification of Ligand-Contacting Peptides by Proteolytic-Excision Mass Spectrometry". JACS 133:14844-14847.
Mossine et al (1994). "The preparation and characterization of some Amadori compounds (1-amino-1-deoxy-D-fructose derivatives) derived from a series of aliphatic w-amino acids". Carbohydrate Research 262:257-270.
Murakami et al (2011). "Synthesis and galectin-binding activities of mercaptododecyl glycosides containing a terminal β-galactosyl group". Bioorganic & Medicinal Chemistry Letters 21: 1265-1269.
Nangia-Makker et al (2002). "Inhibition of Human Cancer Cell Growth and Metastasis in Nude Mice by Oral Intake of Modified Citrus Pectin". Journal of the National Cancer Institute 94: 1854-1862.
Nelson et al (2004). "A Self-Assembled Multivalent Pseudopolyrotaxane for Binding Galectin-1". JACS 126: 11914-11922.
Newton-Northup et al (2012). "Inhibition of metastatic tumor formation in vivo by a bacteriophage display-derived galectin-3 targeting peptide". Clin. Exp. Metastasis 30:119-132.
Nishi et al. (2007), "Role of Galectin-3 in Human Pulmonary Fibrosis". Allergology Internatinal. 56:57-65.
Oberg et al (2011a). "Arene-Anion Based Arginine-Binding Motif on a Galactose Scaffold: Structure-Activity Relationships of Interactions with Arginine-Rich Galeclins". Chem. Eur. J. 17:8139-8144.
Oberg et al (2011b). "Synthesis of 3-amido-3-deoxy-☐-D-talopyranosides: all-cis-substituted pyranosides as lectin inhibitors". Tetrahedron 67:9164-9172.

(56) References Cited

OTHER PUBLICATIONS

Oberg et al (2010). "Copper-Free Huisgen 1,3-Dipolar Cycloaddition to 3-Benzotriazolo-3-Deoxy-β-D-Galactopyranoside—Cyclization of a Galactopyranoside Azide and Benzyne". Trends in Carbohydrate Research 2:1-4.

Oberg et al (2008a). "Arginine Binding Motifs: Design and Synthesis of Galactose-Derived Arginine Tweezers as Galectin-3 Inhibitors". J. Med. Chem. 51:2297-2301.

Oberg et al (2008b). "Protein subtype-targeting through ligand epimerization: Talose-selectivity of galectin-4 and galectin-8". Bioorganic & Medicinal Chemistry Letters 18:3691-3694.

Partridge et al (2004). "Regulation of cytokine receptors by Golgi N-glycan processing and endocytosis". Science 306: 120-124.

Perone et al (2009). "Suppression of autoimmune diabetes by soluble galectin-1". J Immunol 182: 2641-2653.

Pienta et al (1995). "Inhibition of spontaneous metastasis in a rat prostate cancer model by oral administration of modified citrus pectin". J Natl Cancer Inst 87, 348-353.

Platt et al (1992). "Modulation of the Lung Colonization of B16-F1 Melanoma Cells by Citrus Pectin". JNCI 84:439-442.

Pohl et al (1999). "Scope of Multivalent Ligand Function: Lactose-Bearing Neoglycopolymers by Ring-Opening Metathesis Polymerization". Synthesis SI:1515-1519.

Rabinovich et al (2006). "Synthetic lactulose amines: novel class of anticancer agents that induce tumor-cell apoptosis and inhibit galectin-mediated homotypic cell aggregation and endothelial cell morphogenesis". Glycobiology 16:210-220.

Saegusa et al. (2009). "Galectin-3 is critical for the development of the allergic inflammatory response in a mouse model of atopic dermatitis". Am J Pathol 174: 922-931.

Saksida et al (2012). "Galectin-3 Deficiency Protects Pancreatic Islet Cells from Cytokine-Triggered Apoptosis in Vitro". Journal of Cellular Physiology 228:1568-1576.

Salameh et al. (2010). 1H-1,2,3-Triazol-1-yl thiodigalactoside derivatives as high affinity galectin-3 inhibitors. Bioorg Med Chem 18: 5367-5378.

Salameh et al (2006). "Thioureido N-acetyllactosamine derivatives as potent galectin-7 and 9N inhibitors". Bioorganic and Medicinal Chemistry 14:1215-1220.

Salameh et al (2005). "3-(1,2,3-Triazol-1-yl)-1-thio-galactosides as small, efficient, and hydrolytically stable inhibitors of galectin-3". Bioorganic & Medicinal Chemistry 15:3344-3346.

Salomonsson et al (2010). "Monovalent interactions of galectin-1". Biochemistry 49: 9518-9532.

Soomro et al (2011). "CuAAC synthesis of resorcin[4]arene-based glycoclusters as multivalent ligands of lectins". Org. Biomolec. Chem. 9:6587-6597.

Sörme et al (2005). "Structural and thermodynamic studies on cation-π interactions in lectin-ligand Complexes: High-Affinity Galectin-3 Inhibitors through Fine-Tuning of an Arginine-Arene Interaction". JACS 127:1737-1743.

Sörme et al (2004). "Fluorescence polarization as an analytical tool to evaluate galectin-ligand interactions". Anal. Biochem. 334: 36-47.

Sörme et al. (2003a) "Fluorescence polarization to study galectin-ligand interactions". Meth. Enzymol. 362: 504-512.

Sörme et al. (2003b) Design and synthesis of galectin inhibitors. Meth. Enzymol.363: 157-169.

Sörme et al (2002). "Low micromolar inhibitors of galectin-3 based on 3'-derivatization of N-acetyllactosamine". ChemBioChem 3:183-189.

St-Pierre et al (2011). "Galectin-1-Specific Inhibitors as a New Class of Compounds to Treat HIV-1 Infection". Antimicrobial Agents and Chemotherapy 56:154-162.

Tejler et al (2009). "Fragment-based development of triazole-substituted O-galactosyl aldoximes with fragment-induced affinity and selectivity for galectin-3". Organic and Biomolecular Chemistry 7:3982-3990.

Tejler et al (2007). "Synthesis of galactose-mimicking 1H-(1,2,3-triazol-1-yl)-mannosides as selective galectin-3 and 9N inhibitors". Carbohydrate Research 342:1869-1875.

Tejler et al (2006). "Synthesis of multivalent lactose derivatives by 1,3-dipolar cycloadditions: selective galectin-1 inhibition". Carbohydrate Research 341:1353-1362.

Almkvist et al. (2001) Lipopolysaccharide-induced gelatinase granule mobilization primes neutrophils for activation by galectin-3 and f-Met-Leu-Phe. Infect. Immun. 69: 832-837.

André et al (2012). "Synthesis of bivalent lactosides and their activity as sensors for differences between lectins in inter- and intrafamily comparisons". Bioorganic & Medicinal Chemistry Letters 22: 313-318.

André et al (2010). "Glycocluster Design for Improved Avidity and Selectivity in Blocking Human Lectin/Plant Toxin Binding to Glycoproteins and Cells". Molecular Pharmaceutics 7: 2270-2279.

André et al (2009). "Carbamate-Linked Lactose: Design of Clusters and Evidence for Selectivity to Block Binding of Human Lectins to (Neo)Glycoproteins with Increasing Degree of Branching and to Tumor Cells". Bioconjugate Chem. 20: 1716-1728.

André et al (2008). "Calix[n]arene-Based Glycoclusters: Bioactivity of Thiourea-Linked Galactose/Lactose Moieties as Inhibitors of Binding of Medically Relevant Lectins to a Glycoprotein and Cell-Surface Glycoconjugates and Selectivity among Human Adhesion/Growth-Regulatory Galectins". ChemBioChem 9: 1649-1661.

André et al (2007). "Discovery of galectin ligands in fully randomized combinatorial one-bead-one-compound (glyco) peptide libraries". Bioorganic & Medicinal Chemistry Letters 17: 793-798.

André et al (2006). "Glycosyldisulfides from dynamic combinatorial libraries as O-glycoside mimetics for plant and endogenous lectins: Their reactivities in solid-phase and cell assays and conformational analysis by molecular dynamics simulations". Bioorganic & Medicinal Chemistry 14: 6314-6326.

André et al (2005). "Identification of peptide ligands for malignancy- and growth-regulating galectins using random phage-display and designed combinatorial peptide libraries". Bioorganic & Medicinal Chemistry 13: 563-573.

André et al (2004). "Persubstituted Cyclodextrin-Based Glycoclusters as Inhibitors of Protein-Carbohydrate Recognition Using Purified Plant and Mammalian Lectins and Wild-Type and Lectin-Gene-Transfected Tumor Cells as Targets". Bioconjugate Chem. 15: 87-98.

André et al (2003). "First demonstration of differential inhibition of lectin binding by synthetic tri- and tetravalent glycoclusters from cross-coupling of rigidified 2-propynyl lactoside". Org. Biomol. Chem. 1: 3909-3916.

André et al (2001). "Wedgelike Glycodendrimers as Inhibitors of Binding of Mammalian Galectins to Glycoproteins, Lactose Maxiclusters, and Cell Surface Glycoconjugates". ChemBioChem 2: 822-830.

André et al (1999). "Lactose-containing starburst dendrimers: influence of dendrimer generation and binding-site orientation of receptors (plant/animal lectins and immunoglobulins) on binding properties". Glycobiology 9: 1253-1261.

Arnusch et al (2004). "Interference of the galactose-dependent binding of lectins by novel pentapeptide ligands". Bioorganic & Medicinal Chemistry14:1437-1440.

Arsenijevic et al (2012). "The role of Galectin 3 in Con A induced liver injury". Immunology 137:311.

Ballell et al., (2006). "A new chemical probe for the detection of the cancer-linked galectin-3". Org. Biomol. Chem. 4:4387-4394.

Barondes et al. (1994). "Galectins. Structure and function of a large family of animal lectins". J. Biol. Chem. 269:20807-20810.

Bartoloni et al (2013). "Targeting Matrix Metalloproteinases: Design of a Bifunctional Inhibitor for Presentation by Tumour-Associated Galectins". Chemistry—A European Journal 19: 1896-1902.

Belitsky et al (2007). "Multivalent Interactions between Lectins and Supramolecular Complexes: Galectin-1 and Self-Assembled Pseudopolyrotaxanes". Chemistry & Biology 14: 1140-1151.

Blois et al. (2007). A pivotal role for galectin-1 in fetomatemal tolerance. Nat Med 13: 1450-1457.

(56) References Cited

OTHER PUBLICATIONS

Bum-Erdene et al (2013). "Investigation into the Feasibility of Thioditaloside as a Novel Scaffold for Galectin-3-Specific Inhibitors". ChemBioChem 14:1331-1342.

Chen et al. (2012). "Targeting Galectin-1 and Galectin-3 Attenuates VEGF-A-induced Angiogenesis". Mol. Biol. Cell (suppl), Abstract No. 2695.

Chen et al (2013). "TDX, a galectin-1 and galectin-3-specific inhibitor mitigates VEGF-A-induced angiogenesis". FASEB J 27: 828.1.

Chua et al. (2005). "Pulmonary Fibrosis". Am J Respir Cell Mol Biol 33: 9-13.

Collins et al (2012). "Taloside Inhibitors of Galectin-1 and Galectin-3". Chem. Biol. Drug Des. 79:339-346.

Cumpstey et al. (2005a). "Synthesis of a phenyl thio-β-D-galactopyranoside library from 1,5-difluoro-2,4-dinitrobenzene: discovery of efficient and selective monosaccharide inhibitors of galectin-7". Org. Biomol. Chem. 3: 1922-1932.

Cumpstey et al. (2005b). "C2-Symmetrical thiodigalactoside bis-benzamido derivatives as high-affinity inhibitors of galectin-3: Efficient lectin inhibition through double arginine-arene interactions". Angew. Chem. Int. Ed. 44: 5110-5112.

Cumpstey et al (2007). "Studies of arginine-arene interactions through synthesis and evaluation of a series of Galectin-Binding Aromatic Lactose Esters". ChemBioChem 8:1389-1398.

Cumpstey et al. (2008). "Double affinity amplification of galectin-ligand interactions through arginine-arene interactions: Synthetic, thermodynamic, and computational studies with aromatic diamido-thiodigalactosides". Chem. Eur. J. 14: 4233-4245.

Dam et al. (2008). "Effects of clustered epitopes in multivalent ligand-receptor interactions". Biochemistry 47: 8470-8476.

David (2004). "Design of a multivalent galactoside ligand for selective targeting of HPMA copolymer-doxorubicin conjugates to human colon cancer cells". European Journal of Cancer 40: 148-157.

Delacour et al. (2007). "Apical Sorting by Galectin-3-Dependent Glycoprotein Clustering". Traffic 8: 379-388.

Delaine et al. (2008). "Galectin-Inhibitory Thiodigalactoside Ester Derivatives Have Anti-Migratory Effects in Cultured Lung and Prostate Cancer Cells". J Med Chem 51; 8109-8114.

Demotte et al (2010). "A Galectin-3 Ligand Corrects the Impaired Function of Human CD4 and CD8 Tumor-Infiltrating Lymphocytes and Favors Tumor Rejection in Mice". Cancer Res. 70:7476-7488.

Dings et al (2013). "Structure-Based Optimization of Angiostatic Agent 6DBF7, an Allosteric Antagonist of Galectin-1". J. Pharmacol. Exp. Ther. 344 589-599.

Dings et al (2012). "Antitumor Agent Calixarene 0118 Targets Human Galectin-1 as an Allosteric Inhibitor of Carbohydrate Binding". J. Med. Chem. 55:5121-5129.

Dings et al (2010). "Inhibiting Tumor Growth by Targeting Tumor Vasculature with Galectin-1 Antagonist Anginex Conjugated to the Cytotoxic Acylfulvene, 6-Hydroxylpropylacytfulvene". Bioconjugate Chem. 21:20-27.

Dings et al (2008). "Ovarian tumor growth regression using a combination of vascular targeting agents anginex or topomimetic 0118 and the chemotherapeutic irofulven". Cancer Letters 265: 270-280.

Dings et al (2003). "Anti-tumor activity of the novel angiogenesis inhibitor anginex". Cancer Letters 194:55-66.

Disney et al (2007). "Supra molecular Recognition of Galectin 1". Chemistry & Biology 14: 1095-1097.

Fort et al (2006). "Screening for Galectin-3 ilnhibitors from Synthetic Lacto-N-biose Libraries Using Microscale Affinity Chromatography Coupled to Mass Spectrometry". J. Org. Chem. 71: 7146-7154.

Garner et al. (2008). "Galectin-glycan lattices regulate cell-surface glycoprotein organization and signalling". Biochem Soc Trans 36: 1472-1477.

Giguere et al (2011). "Inhibitory potential of chemical substitutions at bioinspired sites of ? β-D-galactopyranose on neoglycoprotein/cell surface binding of two classes of medically relevant lectins". Bioorg. Med. Chem. 19:3280-3287.

Giguere et al (2008). "Synthesis of stable and selective inhibitors of human galectins-1 and -3". Bioorg. Med. Chem., 16:7811-7823.

Giguere et al. (2006a). Carbohydrate triazoles and isoxazoles as inhibitors of galectins-1 and -3. Chem Commun: 2379-2381.

Giguere et al (2006b). "Aryl O- and S-galactosides and lactosides as specific inhibitors of human galectins-1 and -3: Role of electrostatic potential at O-3". Bioorg. Med. Chem. 16:1668-1672.

Glinsky et al (2009). "Synthetic Galectin-3 Inhibitor Increases Metastatic Cancer Cell Sensitivity to Taxol-Induced Apoptosis In Vitro and In Vivo". Neoplasia 11: 901-909.

Glinsky et al (1996). "Inhibition of Human Breast Cancer Metastasis in Nude Mice by Synthetic Glycoamines". Cancer Res. 56:5319-5324.

Gouin et al (2010). "Multimeric Lactoside "Click Clusters" as Tools to Investigate the Effect of Linker Length in Specific Interactions with Peanut Lectin, Galectin-1, and -3". ChemBioChem 11:1430-1442.

Guha et al (2013). "Cod glycopeptide with picomolar affinity to galectin-3 suppresses T-cell apoptosis and prostate cancer metastasis". Proc. Natl. Acad. Sci. 110: 5052-5057.

Huflejt et al (2004). "Galectin-4 in normal tissues and cancer". Glycoconj. J. 20: 247-255.

* cited by examiner

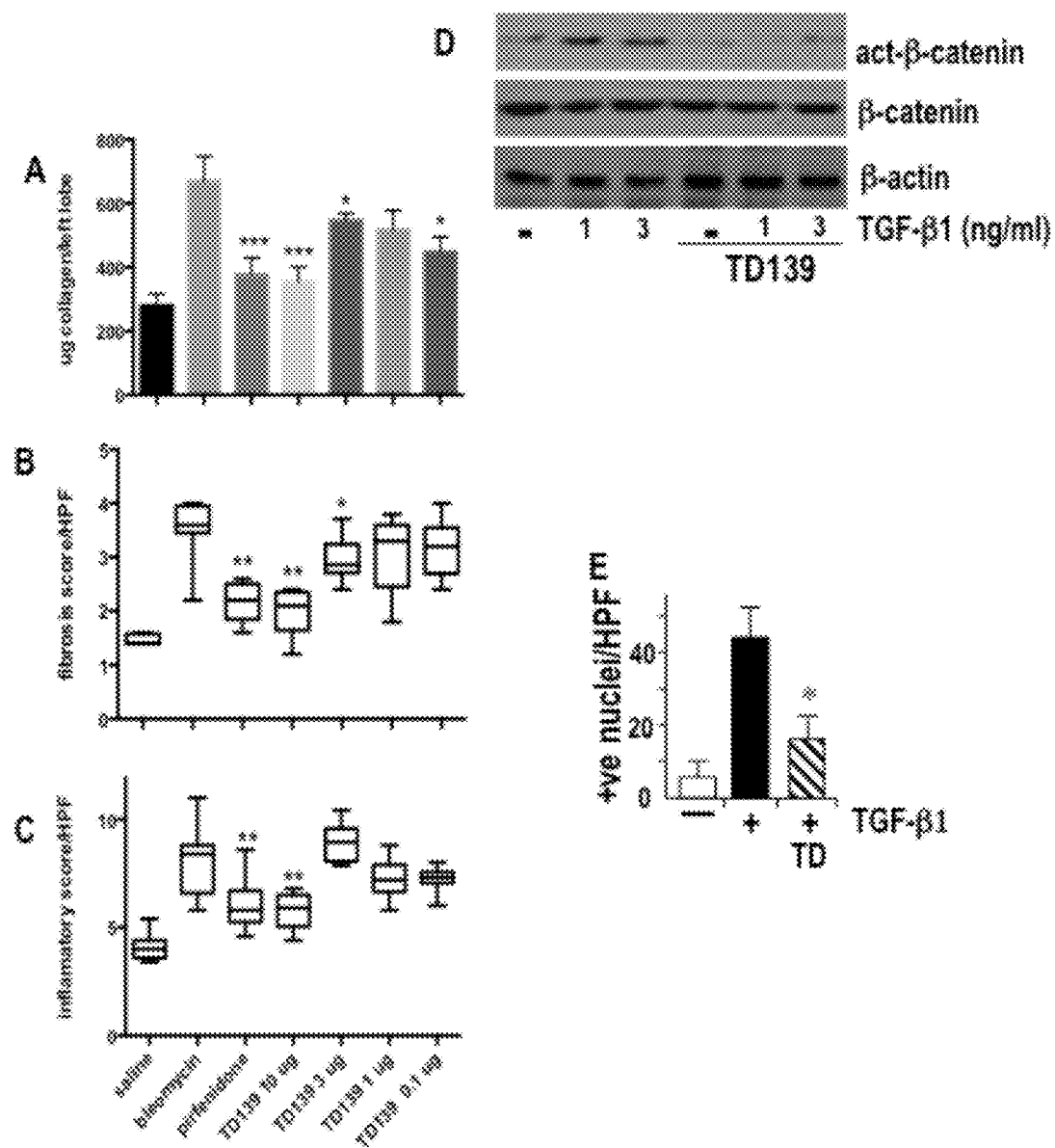

SEQUENCE LISTING

```
<160> NUMBER OF SEQ ID NOS: 9

<210> SEQ ID NO 1
<211> LENGTH: 12
<212> TYPE: PRT
<213> ORGANISM: Unknown
<220> FEATURE:
<223> OTHER INFORMATION: Exemplary epitopes from the N-terminus of
      galectin-3

<400> SEQUENCE: 1

Met Ala Asp Asn Phe Ser Leu His Asp Ala Leu Ser
1               5                   10

<210> SEQ ID NO 2
<211> LENGTH: 14
<212> TYPE: PRT
<213> ORGANISM: Unknown
<220> FEATURE:
<223> OTHER INFORMATION: Exemplary epitopes from the N-terminus of
      galectin-3
```

<400> SEQUENCE: 2

Met Ala Asp Asn Phe Ser Leu His Asp Ala Leu Ser Gly Ser
1               5                   10

<210> SEQ ID NO 3
<211> LENGTH: 10
<212> TYPE: PRT
<213> ORGANISM: Unknown
<220> FEATURE:
<223> OTHER INFORMATION: Exemplary epitopes from the N-terminus of
      galectin-3

<400> SEQUENCE: 3

Trp Gly Asn Gln Pro Ala Gly Ala Gly Gly
1               5                   10

<210> SEQ ID NO 4
<211> LENGTH: 16
<212> TYPE: PRT
<213> ORGANISM: Unknown
<220> FEATURE:
<223> OTHER INFORMATION: Exemplary epitopes from the N-terminus of
      galectin-3

<400> SEQUENCE: 4

Tyr Pro Gly Ala Pro Gly Ala Tyr Pro Gly Ala Pro Ala Pro Gly Val
1               5                   10                  15

<210> SEQ ID NO 5
<211> LENGTH: 11
<212> TYPE: PRT
<213> ORGANISM: Unknown
<220> FEATURE:
<223> OTHER INFORMATION: Exemplary epitopes from the N-terminus of
      galectin-3

<400> SEQUENCE: 5

Gly Asn Pro Asn Pro Gln Gly Trp Pro Gly Ala
1               5                   10

<210> SEQ ID NO 6
<211> LENGTH: 12
<212> TYPE: PRT
<213> ORGANISM: Unknown
<220> FEATURE:
<223> OTHER INFORMATION: Exemplary epitopes from the N-terminus of
      galectin-3

<400> SEQUENCE: 6

Tyr Pro Ser Ser Gly Gln Pro Ser Ala Thr Gly Ala
1               5                   10

<210> SEQ ID NO 7
<211> LENGTH: 18
<212> TYPE: PRT
<213> ORGANISM: Unknown
<220> FEATURE:
<223> OTHER INFORMATION: Exemplary epitopes from the N-terminus of
      galectin-3

<400> SEQUENCE: 7

Tyr Pro Gly Gln Ala Pro Pro Gly Ala Tyr Pro Gly Gln Ala Pro Pro
1               5                   10                  15

Gly Ala

```
<210> SEQ ID NO 8
<211> LENGTH: 19
<212> TYPE: PRT
<213> ORGANISM: Unknown
<220> FEATURE:
<223> OTHER INFORMATION: Exemplary epitopes from the N-terminus of
      galectin-3

<400> SEQUENCE: 8

Tyr Pro Gly Ala Pro Ala Pro Gly Val Tyr Pro Gly Pro Pro Ser Gly
1               5                   10                  15

Pro Gly Ala

<210> SEQ ID NO 9
<211> LENGTH: 12
<212> TYPE: PRT
<213> ORGANISM: Unknown
<220> FEATURE:
<223> OTHER INFORMATION: Exemplary epitopes from the N-terminus of
      galectin-3

<400> SEQUENCE: 9

Tyr Pro Ser Ser Gly Gln Pro Ser Ala Thr Gly Ala
1               5                   10
```

GALACTOSIDE INHIBITOR OF GALECTINS

TECHNICAL FIELD

The present invention relates to novel compounds, the use of said compounds as medicament and for the manufacture of a medicament for the treatment of pulmonary fibrosis, such as Idiopathic pulmonary fibrosis in mammals. The invention also relates to pharmaceutical compositions comprising said novel compounds. Furthermore the present invention relates to pulmonary administration, in particular the use of nebulizers for providing optimal treatment of IPF. The present invention also relates to a method of monitoring development or progression of pulmonary fibrosis as well as a method of monitoring or predicting exacerbation of symptoms.

BACKGROUND ART

Idiopathic pulmonary fibrosis (IPF) represents a massive worldwide health burden. It is a chronic condition of unknown etiology in which repeated acute lung injury causes progressive fibrosis resulting in destruction of lung architecture, deteriorating lung function with consequent respiratory failure and death. Although idiopathic pulmonary fibrosis (IPF) is the archetypal and most common cause of lung fibrosis, numerous respiratory diseases can progress to pulmonary fibrosis, and this usually signifies a worse prognosis. The median time to death from diagnosis is 2.5 years and the incidence and prevalence of IPF continues to rise. It remains one of the few respiratory conditions for which there are no effective therapies, and there are no reliable biomarkers to predict disease progression. The mechanisms resulting in pulmonary fibrosis are unclear but centre around aberrant wound healing as a consequence of repetitive epithelial injury from an as yet unknown cause. IPF is characterized by fibroblastic foci containing fibroblasts/myofibroblasts which show increased activation response to fibrogenic cytokines such as transforming growth factor-$\beta$1 (TGF-$\beta$1). Given the non-responsiveness of many cases of IPF to current anti-inflammatory treatments the myofibroblasts within fibroblastic foci represent a potential novel therapeutic target. There is a big unmet need for drugs for treatment of Idiopathic pulmonary fibrosis.

The bleomycin model of pulmonary fibrosis is the best characterized rodent model and is the industry standard model. Bleomycin treatment causes oxidant-mediated DNA damage and induces initial lung inflammation followed by progressive fibrosis over 2-4 weeks. When administered during the later phase of the injury the anti-fibrotic potential of novel compounds can be assessed.

Galectin inhibitors, in particular Gal-3 inhibitors have been described by the some of the present inventors in earlier published patent applications. None of these galectin inhibitors have been tested in a bleomycin model. Some of the prior art galectin inhibitors have the following general formulas

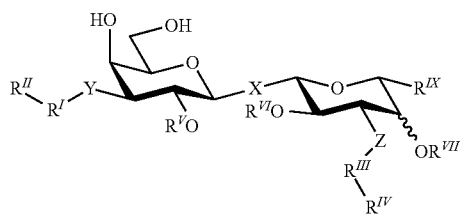

as described in WO/2005/113568, and

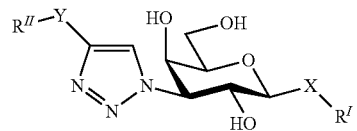

as described in WO/2005/113569, in which Fe can be a D-galactose, and

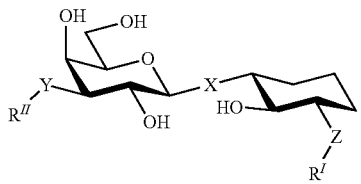

as described in WO/2010/126435.

Furthermore there is a big need for bio-markers for making it less complicated to perform clinical trials in patients with pulmonary fibrosis. No biomarkers exist that are suitable for detection of patients with pulmonary fibrosis or specifically idiopathic pulmonary fibrosis. Similarly, no biomarkers are suitable for prediction of the prognosis for patients with pulmonary fibrosis, for identification of patients with mild or aggressive forms of the disease, for identification of patients with ongoing or preeminent exacerbations, and for tracking the development of the patient's disease level. This makes it very complicated and costly to perform clinical trials of novel treatments in these patients.

SUMMARY OF THE DISCLOSURE

Galectin-3 is a $\beta$-galactoside binding lectin that is highly expressed in fibrotic tissue of diverse etiologies. The role of galectin-3 in bleomycin and TGF-$\beta$1-induced lung fibrosis in mice is examined, and its relevance in human IPF is established. Studies with galectin-3 are described in MacKinnon et al., "Regulation of TGF-$\beta$1 driven lung fibrosis by galectin-3", Am. J. Respir. Crit. Care Med. 185: 537-546 (2012, originally available online on Nov. 17, 2011).). In particular, it is shown that galectin-3 inhibition may represent a novel therapeutic strategy for treatment of lung fibrosis. A novel compound has been tested and shown to be an inhibitor of galectin-3, in particular, this compound blocked TGF-$\beta$-induced $\beta$-catenin activation in vitro and attenuated the late stage progression of lung fibrosis following bleomycin in vivo.

The publications and other materials, including patents, used herein to illustrate the invention and, in particular, to provide additional details respecting the practice are incorporated by reference in their entirety.

Accordingly, provided is a compound of the general formula (I):

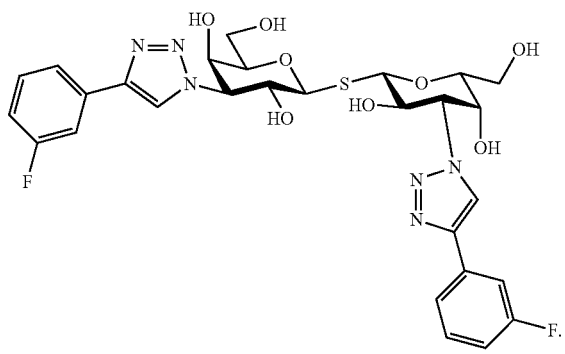

(I)

In a further aspect, provided is a composition, particularly, a pharmaceutical composition comprising the compound of formula (I) and optionally a pharmaceutically acceptable additive, such as carrier or excipient.

The compound of formula (I) is suitable for use in a method for treating pulmonary fibrosis, such as Idiopathic pulmonary fibrosis in a mammal. Typically, such mammal is a human subject. The mode of administration is typically selected from oral, intra venous (i.v.), subcutaneous (s.c.), and pulmonary. In particular the pulmonary route has been shown to provide a considerably longer half-life than the i.v. or s.c. routes in mice. When treating pulmonary fibrosis, in particular IPF, it is important to obtain adequately high local concentrations of the therapeutic in the narrowest parts of the lung tissue, including the bronchioles and the alveoli. Further, it is important that the therapeutic obtains an adequate residence time at the site of action in the lung tissue. Furthermore, since the fibrosis in IPF patients is only located in the lung, it is preferable to obtain a high lung exposure with minimal or no systemic exposure and the use of nebulizers in particular electronic nebulizers of the ultrasonic type is effective. However, cough is a central symptom for patients with pulmonary fibrosis and in particular IPF—a symptom that is likely to be aggravated if an irritant is introduced into the lung. Hence, treatment with a dry powder, such as with a dry powder inhaler or similar, is not suitable for these patients. However, delivering the compound using a nebulizer, such as an electronic nebulizer, is particularly beneficial, since it allows delivery of the compound to the smallest compartments in the lung, without causing any irritation in the lung.

Moreover, in a still further aspect provided is a method for treatment of pulmonary fibrosis, such as Idiopathic pulmonary fibrosis comprising administering to a mammal in need thereof a therapeutically effective amount of the compound of formula (I).

In another aspect, provided is a process of preparing a compound of formula I comprising the step of reacting bis-(3-deoxy-3-azido-β-D-galactopyranosyl) sulfane with 3-fluorophenylacetylene and an amine, such as triethylamine, optionally in the presence of a catalyst, such as Cu(I), in a solvent, such as N,N-dimethylformamide (DMF), resulting in the compound of formula I.

Moreover, the present inventors have discovered that concentrations of the human protein galectin-3 in body fluids or tissues of a human subject can be used to for instance predict or monitor disease progression or therapeutic efficacy in human subjects with pulmonary fibrosis.

Measurement of galectin-3 levels in lung tissue, broncho-alveolar lavage (BAL) fluid, blood, serum or plasma can be used to identify patients with lung fibrosis and to assess the severity of the disease. Longitudinal studies of the levels of galectin-3 in lung tissue, broncho-alveolar lavage fluid, blood, serum or plasma can be used to predict exacerbations and to follow the development of the disease. Hence, measurement of galectin-3 levels in lung tissue, broncho-alveolar lavage fluid, blood, serum or plasma before, during and after completion of a treatment for pulmonary fibrosis can be used to assess the effect of such treatment.

The results of the present inventors demonstrate that serum galectin-3 levels may help distinguish patients with usual interstitial pneumonia (UIP) from patients with non-specific interstitial pneumonia (NSIP) and identify patients undergoing an acute exacerbation of their IPF.

In a further aspect the present invention relates to a method of diagnosing pulmonary fibrosis in a human subject comprising a) measuring a galectin-3 level (e.g. concentration) in a body sample from the human subject using a suitable test method, b) comparing the galectin-3 level to a predetermined reference level, and c) determining whether the galectin-3 level is indicative of diagnosing the subject with pulmonary fibrosis.

In a still further aspect the present invention relates to a method of predicting the prognosis pulmonary fibrosis in a human subject comprising a) measuring a galectin-3 level (e.g. concentration) in a body sample from the human subject using a suitable test method, and b) determining whether the galectin-3 level is indicative of a poor prognosis or not for the human subject.

In a further aspect the present invention relates to a method of monitoring development or progression of pulmonary fibrosis in a human subject, comprising a) measuring a galectin-3 level in a body sample from the subject at least two times with sufficient interval(s) to measure a clinically relevant change, b) comparing the galectin-3 level to a predetermined reference level, and repeating steps a) and b) one or more times to monitor the development or progression of pulmonary fibrosis in the human subject.

In a still further aspect the present invention relates to a method of monitoring or predicting exacerbation of symptoms in a human subject with pulmonary fibrosis comprising a) measuring a galectin-3 level (e.g. concentration) in a body sample from the human subject using a suitable test method, b) comparing the galectin-3 level to a predetermined reference level, and c) determine the presence or absence of a galectin-3 level indicative of the development or progression of exacerbation of symptoms.

In a further aspect the present invention relates to a method for treatment of pulmonary fibrosis, such as Idiopathic pulmonary fibrosis, in a human subject having a galectin-3 level indicative of pulmonary fibrosis or exacerbation of symptoms comprising administering to a human subject a therapeutically effective amount of a galectin-3 inhibitor.

Any one of the above methods can include the step of transmitting, displaying, storing, or printing; or outputting to a user interface device, a computer readable storage medium, a local computer system or a remote computer system, information related to the likelihood of developing pulmonary fibrosis in the subject or for characterization of the degree of severity of the pulmonary fibrosis in said subject.

Accordingly, disclosed herein, inter alia are the following embodiments:

1. A compound of the general formula (I):

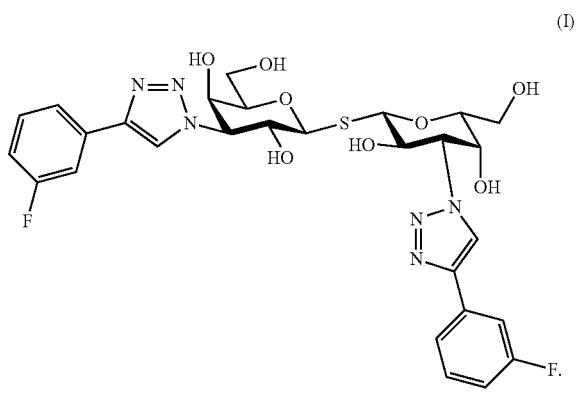

2. The compound of embodiment 1 selected from bis(3-deoxy-3-(3-fluorophenyl-1H-1,2,3-triazol-1-yl)-β-D-galactopyranosyl) sulfane as the free form.

3. The compound according to any one of embodiments 1-2, for use as a medicament.

4. A pharmaceutical composition comprising the compound of any one of embodiments 1-3 and optionally a pharmaceutically acceptable additive, such as a carrier or an excipient.

5. The pharmaceutical composition of embodiment 4 wherein the composition is administered by the pulmonary route.

6. The pharmaceutical composition of embodiment 5 wherein administration by the pulmonary route is selected from a nebulizer such as an ultrasonic nebulizer or a jet nebulizer.

7. The compound of any one of the embodiments 1-3 for use in a method for treating pulmonary fibrosis, such as Idiopathic pulmonary fibrosis in a mammal.

8. The compound of embodiment 7, wherein the compound is administered by the pulmonary route.

9. The compound of embodiment 8, wherein administration by the pulmonary route is selected from a nebulizer such as an ultrasonic nebulizer or a jet nebulizer.

10. The compound of embodiment 7, 8 or 9 wherein said mammal is a human subject.

11. A method for treatment of pulmonary fibrosis, such as Idiopathic pulmonary fibrosis comprising administering to a mammal in need thereof a therapeutically effective amount of the compound of any one of embodiments 1-3.

12. The method of embodiment 11, wherein the compound of any one of embodiments 1-3 is administered by the pulmonary route.

13. The method of embodiment 12, wherein administration by the pulmonary route is selected from a nebulizer such as an ultrasonic nebulizer or a jet nebulizer.

14. A process of preparing a compound of formula I comprising a step of reacting bis-(3-deoxy-3-azido-β-D-galactopyranosyl) sulfane with 3-fluorophenylacetylene and an amine in a solvent, resulting in the compound of formula I.

15. The process of embodiment 14 wherein the amine is triethylamine, a catalyst is present, such as Cu(I), and the solvent is an organic solvent, such as N,N-dimethylformamide (DMF).

16. A nebulizer device for pulmonary administration comprising a compound of any one of embodiments 1-3.

17. The nebulizer device of embodiment 16, wherein the compound is bis(3-deoxy-3-(3-fluorophenyl-1H-1,2,3-triazol-1-yl)-β-D-galactopyranosyl) sulfane as the free form.

18. The nebulizer of embodiment 16 or 17 which is selected from an ultrasonic nebulizer or a jet nebulizer.

19. A dry powder device for pulmonary administration comprising a compound of any one of embodiments 1-3.

20. The dry powder device of embodiment 19, wherein the compound is bis(3-deoxy-3-(3-fluorophenyl-1H-1,2,3-triazol-1-yl)-β-D-galactopyranosyl) sulfane as the free form.

21. A method of diagnosing pulmonary fibrosis in a human subject comprising a) measuring a galectin-3 level (e.g. concentration) in a body sample from the human subject using a suitable test method, b) comparing the galectin-3 level to a predetermined reference level, and c) determining whether the galectin-3 level is indicative of diagnosing the subject with pulmonary fibrosis.

22. The method of embodiment 21 wherein the indicative level of galectin-3 is at least 22 ng/ml, such as at least 25 ng/ml, such as at least 30 ng/ml, at least 40 ng/ml, at least 50 ng/ml, at least 60 ng/ml, at least 70 ng/ml.

23. A method of predicting the prognosis of pulmonary fibrosis in a human subject comprising a) measuring a galectin-3 level (e.g. concentration) in a body sample from the human subject using a suitable test method, and b) determining whether the galectin-3 level is indicative of a poor prognosis or not for the human subject.

24. The method of embodiment 23 wherein the indicative level of galectin-3 is at least 22 ng/ml, such as at least 25 ng/ml, such as at least 30 ng/ml, at least 40 ng/ml, at least 50 ng/ml, at least 60 ng/ml, at least 70 ng/ml.

25. A method of monitoring development or progression of pulmonary fibrosis in a human subject, comprising a) measuring a galectin-3 level in a body sample from the subject at least two times with sufficient interval(s) to measure a clinically relevant change, b) comparing the galectin-3 level to a predetermined reference level, and repeating steps a) and b) one or more times to monitor the development or progression of pulmonary fibrosis in the human subject.

26. The method of embodiment 25 wherein the time period between two measurements is independently selected from about 2 weeks to 2 years, such as 2 weeks, 4 weeks, 1 month, 2 months, 3 months 6 months, 1 year, or 2 years.

27. The method of embodiment 25 wherein when the indicative level of galectin-3 is below 22 ng/ml treatment of pulmonary fibrosis may be stopped, adjusted or put on hold.

28. The method of embodiment 25 wherein when the indicative level of galectin-3 is at least 22 ng/ml, such as at least 25 ng/ml, such as at least 30 ng/ml, at least 40 ng/ml, at least 50 ng/ml, at least 60 ng/ml, at least 70 ng/ml treatment of pulmonary fibrosis may be initiated or increased.

29. A method of monitoring or predicting exacerbation of symptoms in a human subject with pulmonary fibrosis comprising a) measuring a galectin-3 level (e.g. concentration) in a body sample from the human subject using a suitable test method, b) comparing the galectin-3 level to a predetermined reference level, b) determine the presence or absence of a galectin-3 level indicative of the development or progression of exacerbation of symptoms, and c) repeating steps a) and b) to monitor or predict the development or progression of the exacerbation of symptoms in the human subject.

30. The method of embodiment 29 wherein when the indicative level of galectin-3 is below 22 ng/ml treatment of pulmonary fibrosis may be stopped, adjusted or put on hold.

31. The method of embodiment 29 wherein when the indicative level of galectin-3 is at least 22 ng/ml, such as at least 25 ng/ml, such as at least 30 ng/ml, at least 40 ng/ml, at least 50 ng/ml, at least 60 ng/ml, at least 70 ng/ml treatment of pulmonary fibrosis is initiated or increased. 32. The method of embodiment 29 wherein when the indicative level of galectin-3 is at least 50 ng/ml, at least 60 ng/ml, at least 70 ng/ml prophylactic treatment of exacerbation of symptoms is initiated or increased.

33. The method of any one of embodiments 17-28 wherein the pulmonary fibrosis is idiopathic pulmonary fibrosis.

34. The method of any one of embodiments 21-33 wherein the subject is diagnosed with mild, moderate or aggressive forms of pulmonary fibrosis according to the level of galectin-3.

35. The method of any one of embodiments 21-34 wherein in step a) further bio-markers are measured which markers are relevant for pulmonary fibrosis, including markers linked to Galectin-3 levels, leading to a more accurate diagnosis, prognosis, and/or monitoring.

36. The method of embodiment 35 wherein the biomarkers are selected from MMP7, perDLCO, KL-6, SP-A, MMP-7, CCL-18, IL13, CC-chemokines, IL10, IL1 receptor antagonist, CCL2, Calgranulin B (S100A9 or MRP14), macrophage migration inhibitory factor (MIF), pro-collagen, pro-collagen 3.

37. The method of embodiment 35 wherein the biomarkers are selected from analysis of the presence and frequency of certain cell types in body fluids from said human subject.

38. The method of embodiment 36 wherein the biomarkers are selected from analysis of the presence and frequency of fibrocytes and T-cell subpopulations in body fluids from said human subject.

39. The method of any one of embodiments 21-38 wherein the predetermined reference level for galectin-3 is in the range from about 10.0 ng/mL to about 25.0 ng/mL, such as in the range from about 13.0 ng/mL to about 19.2 ng/mL.

40. The method of any one of embodiments 21-39 wherein the body sample is selected from blood, serum, plasma, broncho-alveolar lavage fluid, lung tissue.

41. The method of any one of embodiments 21-40 wherein the suitable test method is selected from an immunoassay, an immunohistochemical assay, a colorimetric assay, a turbidimetric assay, and flow cytometry.

42. The method of embodiment 17 or 29, wherein the subject has a galectin-3 blood concentration determined to be within a target range.

43. The method of embodiment 42, wherein the target range is from about 10 ng/ml to about 70 ng/ml.

44. A method for treatment of pulmonary fibrosis, such as Idiopathic pulmonary fibrosis in a human subject having a galectin-3 level indicative of pulmonary fibrosis or exacerbation of symptoms comprising administering to a human subject a therapeutically effective amount of a galectin-3 inhibitor.

45. The method of embodiment 40 wherein the galectin-3 inhibitor is selected from the compound of any one of embodiments 1-3.

46. The method of embodiment 44 wherein the indicative level of galectin-3 is at least 22 ng/ml, such as at least about 25 ng/ml, such as at least about 30 ng/ml, at least about 40 ng/ml, at least about 50 ng/ml, at least about 60 ng/ml, at least about 70 ng/ml.

47. The method of embodiment 44 comprising the additional step of monitoring the subject's galectin-3 blood level after the therapy is initiated.

Accordingly, also disclosed herein, inter alia are the following embodiments:

1. A compound of the general formula (I):

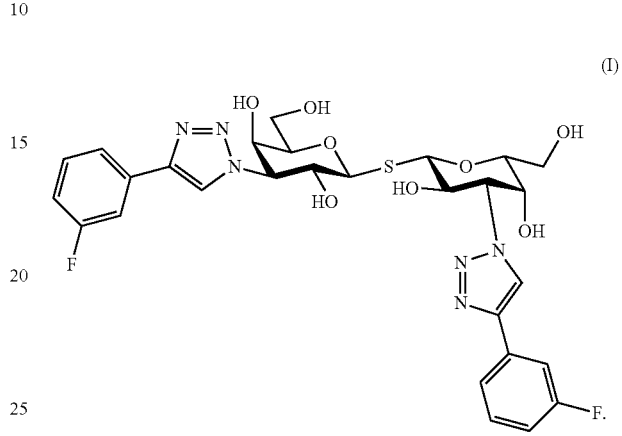

2. The compound of embodiment 1 selected from bis(3-deoxy-3-(3-fluorophenyl-1H-1,2,3-triazol-1-yl)-β-D-galactopyranosyl) sulfane as the free form.

3. A composition comprising the compound of embodiment 1 and optionally a pharmaceutically acceptable additive.

4. A method for treatment of pulmonary fibrosis comprising administering to a mammal in need thereof an amount of the compound of embodiment 1 effective to treat said pulmonary fibrosis.

5. The method of embodiment 4, wherein said compound is administered by the pulmonary route.

6. A process of preparing a compound of formula I comprising a step of reacting bis-(3-deoxy-3-azido-β-D-galactopyranosyl) sulfane with 3-fluorophenylacetylene and an amine in a solvent, resulting in the compound of formula I.

7. The process of embodiment 5, wherein the amine is triethylamine, a catalyst is present, such as Cu(I), and the solvent is an organic solvent, such as N,N-dimethylformamide (DMF).

8. A device for pulmonary administration, wherein said device is a nebulizer or dry powder device comprising the compound of embodiment 1.

9. The device of embodiment 8, wherein said device is a nebulizer which is selected from an ultrasonic nebulizer or a jet nebulizer.

10. A method of detecting the presence and/or extent of pulmonary fibrosis to diagnose pulmonary fibrosis and/or predict the prognosis of pulmonary fibrosis in a human subject comprising a) measuring a galectin-3 level in a body sample from the human subject using a suitable test method, b) comparing the galectin-3 level to a predetermined reference level, and c) determining whether the galectin-3 level is indicative of diagnosing the subject with pulmonary fibrosis.

11. The method of embodiment 10, wherein the indicative level of galectin-3 is at least about 22 ng/ml.

12. A method of monitoring development or progression of or exacerbation of symptoms of pulmonary fibrosis in a human subject, comprising a) measuring a galectin-3 level in a body sample from the subject at least two times with sufficient interval(s) to measure a clinically relevant change, b) comparing the galectin-3 level to a predetermined reference level, and repeating steps a) and b) one or more times to monitor the development or progression of pulmonary fibrosis in the human subject.

13. The method of embodiment 12, wherein the time period between two measurements is independently selected from about 2 weeks to about 2 years.

14. The method of embodiment 12, wherein when the level of galectin-3 is below about 22 ng/ml treatment of pulmonary fibrosis is stopped, adjusted or put on hold.

15. The method of embodiment 12, wherein the pulmonary fibrosis is idiopathic pulmonary fibrosis.

16. The method of embodiment 12, wherein the subject is diagnosed with mild, moderate or aggressive forms of pulmonary fibrosis according to the level of galectin-3.

17. The method embodiment 12, wherein in step a) further bio-markers are measured, where said markers are linked to Galectin-3 levels.

18. The method of embodiment 17, wherein the biomarkers are selected from MMP7, perDLCO, KL-6, SP-A, MMP-7, CCL-18, IL13, CC-chemokines, IL10, IL1 receptor antagonist, CCL2, Calgranulin B (S100A9 or MRP14), macrophage migration inhibitory factor (MIF), pro-collagen, pro-collagen 3.

19. The method of embodiment 17, wherein the biomarkers are selected from analysis of the presence and frequency of certain cell types in body fluids from said human subject.

20. The method of embodiment 17, wherein the biomarkers are selected from analysis of the presence and frequency of fibrocytes and T-cell subpopulations in body fluids from said human subject.

21. The method of embodiment 12, wherein the predetermined reference level for galectin-3 is in the range from about 10.0 ng/mL to about 25.0 ng/mL.

22. The method of embodiment 12, wherein the body sample is selected from blood, serum, plasma, bronchoalveolar lavage fluid, lung tissue.

23. The method of embodiment 10, wherein the suitable test method is selected from an immunoassay, an immunohistochemical assay, a colorimetric assay, a turbidimetric assay, and flow cytometry.

24. The method of embodiment 10, wherein the subject has a galectin-3 blood concentration determined to be within a target range from about 10 ng/ml to about 70 ng/ml.

25. The method of embodiment 12, wherein the subject has a galectin-3 blood concentration determined to be target range is from about 10 ng/ml to about 70 ng/ml.

BRIEF DESCRIPTION OF THE FIGURES

FIG. 1 shows (A) Total lung collagen measured by Sircol assay; (B) Fibrosis score; and (C) Inflammatory score. Results represent the mean and SEM (A) or box and whiskers (median, interquartile range, minimum to maximum, B and C) of n=8 mice per group (n=7 bleo). *P<0.005, P<0.01, *P<0.05. FIG. 1D shows the effect of treatment of primary alveolar epithelial cells from WT mice with TGF-β1 in the presence or absence of 10 μM TD139 on active β-catenin, total β-catenin and β-actin using western blot analysis. In FIG. 1E, beta-catenin activation in vivo was assessed by scoring sections of bleomycin treated mouse lung (control and 10 ug TD139 treated) stained with an anti-active beta catenin.

DETAILED DESCRIPTION

In a broad aspect, provided is a compound of the general formula (I):

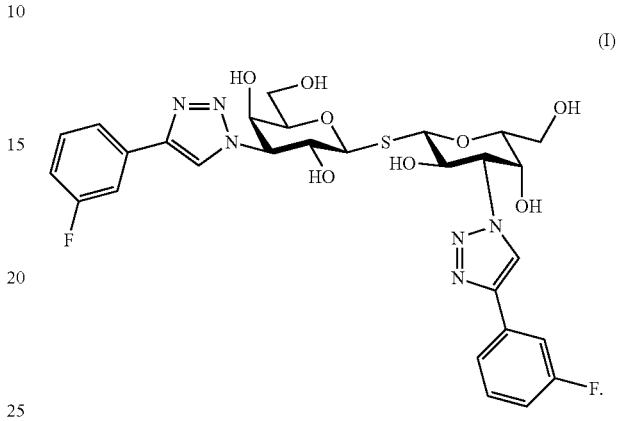

The compound of formula (I) has the chemical name (IUPAC) bis(3-deoxy-3-(3-fluorophenyl-1H-1,2,3-triazol-1-yl)-β-D-galactopyranosyl) sulfane, and as used herein is intended to cover the compound of formula (I) in any possible form, such as solid or liquid, a salt, a solvate, or in free form.

Typically, the compound of formula (I) is bis(3-deoxy-3-(3-fluorophenyl-1H-1,2,3-triazol-1-yl)-β-D-galactopyranosyl) sulfane as the free form. In a further embodiment the compound of formula (I) is bis(3-deoxy-3-(3-fluorophenyl-1H-1,2,3-triazol-1-yl)-β-D-galactopyranosyl) sulfane as the free form without any solvate, such as anhydrated.

In a further embodiment the compound of formula (I) is bis(3-deoxy-3-(3-fluorophenyl-1H-1,2,3-triazol-1-yl)-β-D-galactopyranosyl) sulfane on amorphous form.

In a further embodiment the compound of formula (I) is bis(3-deoxy-3-(3-fluorophenyl-1H-1,2,3-triazol-1-yl)-β-D-galactopyranosyl) sulfane on a crystalline form.

In a still further embodiment, the compound of formula (I) is useful for treating pulmonary fibrosis, and therefore is suitable for use as a medicament.

In a further aspect, provided is a compound of formula (I) for use in a method for treating pulmonary fibrosis, such as Idiopathic pulmonary fibrosis in a mammal. Such a mammal is typically a human subject, preferably a human subject diagnosed with IPF.

In a still further aspect, provided is a method for treatment of pulmonary fibrosis, such as Idiopathic pulmonary fibrosis comprising administering to a mammal a therapeutically effective amount of a compound of formula (I).

When the compounds and pharmaceutical compositions herein disclosed are used for the above treatment, a therapeutically effective amount of at least one compound is administered to a mammal in need of said treatment.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular a human being, but it may also include animals, such as dogs, cats, cows, sheep and pigs.

The term "a therapeutically effective amount" of a compound of formula (I) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the compound of formula (I) and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (I) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compound as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Thus, in a still further aspect provided is a composition, particularly a pharmaceutical composition for intrapulmonary administration. Typically, such composition is delivered by a nebulizer or inhaler, preferably a nebulizer.

Boehringer Ingelheim provided a new technology in 1997 named Raspimat which is a mechanical nebulizer of the soft mist inhaler type. This mechanical nebulizer is operated by hand without any need for a gas propellant and no need for electrical power. Another mechanical nebulizer is a human powered nebulizer developed by a team from Marquette University. This nebulizer can by operated by an electrical compressor, but it is also suitable for simple mechanical pumps in order to provide a mist into the lungs of patients. Further nebulizers of the electrical type are ultrasonic nebulizers based on the vibrating mesh technology developed by inter alia PARI, Respironics, Omron, Beurer, Aerogen, or ultrasonic nebulizers based on an electronic oscillator that generate a high frequency ultrasonic wave developed by inter alia Omron and Beurer. A further electrical nebulizer is a jet nebulizer also known as atomizers.

In a further embodiment the nebulizer is selected from a mechanical nebulizer, such as a soft mist inhaler or a human powered nebulizer. In another embodiment the nebulizer is selected from an electrical nebulizer, such as a nebulizer based on ultrasonic vibrating mesh technology, a jet nebulizer, or an ultrasonic wave nebulizer. Particular suitable nebulizers are based on vibrating mesh technology such as eFlow from PARI. When treating pulmonary fibrosis, in particular IPF, it is important to obtain adequately high local concentrations of the therapeutic in the narrowest parts of the lung tissue, including the bronchioles and the alveoli. Further, it is important that the therapeutic obtains an adequate residence time at the site of action in the lung tissue. However, cough is a central symptom for patients with pulmonary fibrosis and in particular IPF—a symptom that is likely to be aggravated if an irritant is introduced into the lung. Hence, treatment with a dry powder, such as with a dry powder inhaler or similar, is not suitable for these patients. However, delivering the compound using a nebulizer, such as an electronic nebulizer, is particularly beneficial, since it allows delivery of the compound to the smallest compartments in the lung, without causing any irritation in the lung. Such relevant nebulizer systems are described in published patent applications US20040089295, US20050056274, US20060054166, US20060097068, US20060102172, US20080060640, US20110155768, and US20120167877, all of which are incorporated herein by reference. Other suitable nebulizers are Tyvaso inhalation system from United Therapeutics, Allera nebulizer system from Gilead, Bronchitol inhaler from Pharmaxis, Diskhaler from GSK, jet and ultrasonic nebulizers from Actelion and Profile Pharma.

The following characteristics are required for the pulmonary delivery device: It should be able to provide a specific dose accurately and repeatedly. It should be able to provide 2 or more different dose levels, for instance through repeated dosing or by adjusting the dose provide to the patient. The device should ensure that the drug is delivered to the bronchiolar space or preferably to the bronchiolar and the alveolar space of the lung preferably uniformly over the lung tissue. Hence, the device should generate aerosols or dry powder of an adequately small size to ensure this delivery, while not delivering particles so small that they are immediately exhaled and thus not remaining in the lung tissue.

Inhalation nebulizers deliver therapeutically effective amounts of pharmaceuticals by forming an aerosol which includes particles of a size that can easily be inhaled. The aerosol can be used, for example, by a patient within the bounds of an inhalation therapy, whereby the therapeutically effective pharmaceutical or drug reaches the patient's respiratory tract upon inhalation.

A variety of inhalation nebulizers are known. EP 0 170 715 A1 uses a compressed gas flow to form an aerosol. A nozzle is arranged as an aerosol generator in an atomizer chamber of the inhalation nebulizer and has two suction ducts arranged adjacent a compressed-gas channel. When compressed air flows through the compressed-gas channel, the liquid to be nebulized is drawn in through the suction ducts from a liquid storage container.

EP 0 432 992 A discloses a nebulizer comprising an aerosol generator having a liquid storage container, a perforate membrane and a vibrator. The vibrator is operable to vibrate the membrane such that it dispenses an aerosol from a liquid through holes provided in the membrane.

U.S. Pat. No. 5,918,593 relates to ultrasonic nebulizers generating an aerosol by interaction between an amount of liquid and a piezo electric element. Droplets of various sizes are expelled from a surface of a liquid bulk when vibrational energy is transferred from the piezo element to the liquid. The droplets thus generated are filtered in an atomizer chamber since oversized droplets have to be removed from the droplets expelled from the surface in order to generate an aerosol for inhalation by a patient. This nebulizer is representative of continuously operating inhalation nebulizers, in which the aerosol generator produces an aerosol not only during inhalation but also while the patient exhales. The aerosol produced by the aerosol generator is actually inhaled by the patient only in the inhalation phase, while any aerosol produced at other times is lost.

Dry powder inhalers, such as metered dose medicament inhalers are well known for dispensing medicament to the lungs of a patient. Some previous inhalers have comprised a pressurized aerosol dispensing container, wherein the aerosols contain gas propellants in which the powdered medicament is suspended. Upon actuation, the aerosol contents are expelled, through a metering valve, and into the lungs of the patient.

Several types of non-aerosol, breath actuated dry powder inhalers have therefore been provided. For example, U.S. Pat. No. 5,503,144 to Bacon, shows a breath-actuated dry-powder inhaler. The device includes a dry powder reservoir for containing a dry powdered medicament, a metering chamber for removal of the powdered medicament from the reservoir in discrete amounts, and an air inlet for entraining the removed powdered medicament through a mouthpiece upon patient inhalation.

U.S. Pat. No. 5,458,135 discloses a method and apparatus for producing an aerosolized dose of a medicament for subsequent inhalation by a patient. The method comprises first dispersing a preselected amount of the medicament in a predetermined volume of gas, usually air. The dispersion may be formed from a liquid or a dry powder. The method relies on flowing substantially the entire aerosolized dose into a chamber that is initially filled with air and open through a mouthpiece to the ambient. After the aerosolized medicament has been transferred to the chamber, the patient will inhale the entire dose in a single breath.

U.S. Pat. No. 6,065,472 discloses a powder inhalation device comprising a housing containing a pharmacologically active compound, a conduit with an outlet extending into the housing through which a user can inhale to create an airflow through the conduit, a dosing unit for delivering a dose of the compound to the conduit and baffles arranged within the said conduit to aid disintegration of powder agglomerates entrained in said airflow.

Regardless of whether an aerosol or non-aerosol inhaler is used, it is of utmost importance that particles of the dispensed dry powder medicament be small enough to ensure the adequate penetration of the medicament into the bronchial region of a patient's lungs during inhalation. However, because the dry powder medicament is composed of very small particles, and often provided in a composition including a carrier such as lactose, non-defined agglomerates or aggregates of the medicament form at random prior to being dispensed. It has therefore been found preferably to provide breath-actuated dry powder inhalers with means for breaking down the agglomerates of medicament or medicament and carrier before inhalation of the medicament.

The composition and particularly pharmaceutical composition may optionally comprise two or more compounds of the present invention. The composition may also be used together with other medicaments within the art for the treatment of related disorders.

The typical dosages of the compounds set forth herein vary within a wide range and depend on many factors, such as the route of administration, the requirement of the individual in need of treatment, the individual's body weight, age and general condition.

The compound of formula (I) may be prepared as described in the experimental section below.

Accordingly, provided is a process of preparing a compound of formula I comprising the step of reacting bis-(3-deoxy-3-azido-β-D-galactopyranosyl) sulfane with 3-fluorophenylacetylene and an amine, such as triethylamine, optionally in the presence of a catalyst, such as Cu(I), in a solvent, such as N,N-dimethylformamide (DMF), resulting in the compound of formula I. In a particular embodiment, provided is a process of preparing a compound of formula I comprising the steps as described in the scheme 1 in the experimental section. Moreover, the present invention relates to a compound of formula (I) obtainable by the step of reacting bis-(3-deoxy-3-azido-β-D-galactopyranosyl) sulfane with 3-fluorophenylacetylene and an amine, such as triethylamine, optionally in the presence of a catalyst, such as Cu(I), in a solvent, such as N,N-dimethylformamide (DMF), resulting in the compound of formula I, such as obtainable by the steps as described in the scheme 1 in the experimental section.

The present invention also relates to a method of diagnosing pulmonary fibrosis in a human subject comprising a) measuring a galectin-3 level in a body sample from the human subject using a suitable test method, b) comparing the galectin-3 level to a predetermined reference level, and c) determining whether the galectin-3 level is indicative of diagnosing the subject with pulmonary fibrosis. Such galectin-3 level is typically the galectin-3 concentration measured in ng/ml in a body sample such as body fluid, e.g. blood, plasma, or serum. Such galectin-3 levels may also be measured as ng/mg in a body sample consisting of tissue, such as lung tissue.

The term "a predetermined reference level" as used herein means a galectin-3 level which is determined through analysis of a large group of human subject which are not suffering from pulmonary fibrosis. Such determination of the predetermined reference level have been investigated in several publications, such as US20120220671 and MacKinnon et al., "Regulation of TGF-β1 driven lung fibrosis by galectin-3", Am. J. Respir. Crit. Care Med. 185: 537-546, Journal of the American College of Cardiology Vol. xx, No. x, 2012, Ho et al., title: "Galectin-3, a Marker of Cardiac Fibrosis, Predicts Incident Heart Failure in the Community" and Clin Res Cardiol (2010) 99:323-328, Lok et al., title: "Prognostic value of galectin-3, a novel marker of fibrosis, in patients with chronic heart failure: data from the DEAL-HF study". Based on these studies, the levels have been determined to be within a concentration range from about 10.0 ng/mL to about 25.0 ng/mL galectin-3. In some populations said range may be from about 13.0 ng/mL to about 19.2 ng/mL galectin-3.

The indicative level is the level of galectin-3, which to the person skilled in the art, such as a physician, provides such person with a tool to set a diagnosis. Typically, the indicative level of galectin-3 is at least 22 ng/ml. In a further embodiment the indicative level of galectin-3 is at least 25 ng/ml, such as at least 30 ng/ml, at least 40 ng/ml, at least 50 ng/ml, at least 60 ng/ml, at least 70 ng/ml.

Furthermore, the present invention relates to a method of predicting a prognosis of pulmonary fibrosis in a human subject comprising a) measuring a galectin-3 level (e.g. concentration) in a body sample from the human subject using a suitable test method, and b) determining whether the galectin-3 level is indicative of a poor prognosis or not for the human subject.

The indicative level is the level of galectin-3, which to the person skilled in the art, such as a physician, provides such person with a tool to predict the prognosis of the subject. Typically, the indicative level of galectin-3 is at least 22 ng/ml. In a further embodiment the indicative level of galectin-3 is at least about 25 ng/ml, such as at least about 30 ng/ml, at least about 40 ng/ml, at least about 50 ng/ml, at least about 60 ng/ml, at least about 70 ng/ml.

As the tracking of the development of the human subject's disease level is desired, it is of great importance to develop a method of monitoring the development, such as improvement or deterioration, or progression of pulmonary fibrosis, e.g. IPF. It is generally very complicated and costly to perform clinical trials of novel treatments in these patients.

Accordingly, the present invention relates to a method of monitoring development or progression of pulmonary fibrosis in a human subject, comprising a) measuring a galectin-3 level in a body sample from the subject at least two times with sufficient interval(s) to measure a clinically relevant change, b) comparing the galectin-3 level to a predetermined reference level, and repeating steps a) and b) one or more times to monitor the development or progression of pulmonary fibrosis in the human subject.

Whether a change is clinically relevant will be determined by a person skilled in the art, in particular a physician. The time period between two measurements (that is the sufficient interval) is independently selected from 2 weeks to 2 years. In individual embodiments such time period between two measurements is selected from 2 weeks, 4 weeks, 1 month, 2 months, 3 months 6 months, 1 year, or 2 years.

When the indicative level of galectin-3 is below 22 ng/ml treatment of pulmonary fibrosis may be stopped, adjusted or put on hold. This is typically determined by the physician.

When the indicative level of galectin-3 is at least about 22 ng/ml treatment of pulmonary fibrosis may be initiated or increased. This is typically determined by the physician. In further embodiments the galectin-3 level is at least about 25 ng/ml, such as at least about 30 ng/ml, at least about 40 ng/ml, at least about 50 ng/ml, at least about 60 ng/ml, or at least about 70 ng/ml. In another embodiment the subject has a galectin-3 blood concentration determined to be within a target range. Typically, such target range is from 10 ng/ml to 70 ng/ml. In a selected or treated human subject, the blood concentration of galectin-3 may be determined to be above a minimum threshold, below a maximum threshold or within a target range defined by a minimum and a maximum threshold. The minimum threshold may be, for example, more than 10 ng/ml; between 10 and 15 ng/ml; between 15 and 20 ng/ml; between 20 and 25 ng/ml; between 25 and 30 ng/ml; or be more than 30 ng/ml. The maximum threshold may be, for example, below 70 ng/ml; below 60 ng/ml; below 40 ng/ml; between 30 and 40 ng/ml; between 25 and 30 ng/ml; between 20 and 25 ng/ml; or between 15 and 20 ng/ml.

In a further aspect the present invention relates to a method of monitoring or predicting exacerbation of symptoms in a human subject with pulmonary fibrosis comprising a) measuring a galectin-3 level (e.g. concentration) in a body sample from the human subject using a suitable test method, b) comparing the galectin-3 level to a predetermined reference level, b) determine the presence or absence of a galectin-3 level indicative of the development or progression of exacerbation of symptoms, and if deemed necessary c) repeating steps a) and b) to monitor or predict the development or progression of the exacerbation of symptoms in the human subject.

When the indicative level of galectin-3 is at least about 22 ng/ml treatment of pulmonary fibrosis may be initiated or increased or it may be decided to monitor the patient more closely to counter the effect of the ongoing or eminent exacerbation, if possible. This is typically determined by the physician. In further embodiments the galectin-3 level is at least about 25 ng/ml, such as at least about 30 ng/ml, at least about 40 ng/ml, at least about 50 ng/ml, at least about 60 ng/ml, or at least about 70 ng/ml. In another embodiment the subject has a galectin-3 blood concentration determined to be within a target range. Typically, such target range is from 10 ng/ml to 70 ng/ml. In a selected or treated human subject, the blood concentration of galectin-3 may be determined to be above a minimum threshold, below a maximum threshold or within a target range defined by a minimum and a maximum threshold. The minimum threshold may be, for example, more than 10 ng/ml; between 10 and 15 ng/ml; between 15 and 20 ng/ml; between 20 and 25 ng/ml; between 25 and 30 ng/ml; or be more than 30 ng/ml. The maximum threshold may be, for example, below 70 ng/ml; below 60 ng/ml; below 40 ng/ml; between 30 and 40 ng/ml; between 25 and 30 ng/ml; between 20 and 25 ng/ml; or between 15 and 20 ng/ml.

As it is desired to prevent or reduce exacerbation of symptoms such prophylactic treatment should be initiated in good time before the level of galectin-3 reaches 70 ng/ml, thus it is preferred to initiate or increase prophylactic treatment of exacerbation of symptoms at a galectin level of least 50 ng/ml, such as at least about 60 ng/ml, e.g. at least about 70 ng/ml.

Typically, the pulmonary fibrosis is idiopathic pulmonary fibrosis (IPF).

In a further embodiment the human subject is diagnosed with mild, moderate or aggressive forms of pulmonary fibrosis according to the level of galectin-3.

Multimarker analysis can be used to improve the accuracy of diagnosis and monitoring. Expression of markers, such as MMP7 and perDLCO has been linked with pulmonary fibrosis (Am J Respir Crit Care Med 185; 2012:A6241)

When measuring the levels of the above markers, corrections for age, gender and concomitant morbidity may be incorporated to improve the accuracy of diagnosis.

Thus, in a further embodiment in step a) further biomarkers are measured which markers are relevant for pulmonary fibrosis, including markers linked to Galectin-3 levels, leading to a more accurate diagnosis, prognosis, and/or monitoring. Typically, such bio-markers are selected from MMP7, perDLCO, KL-6, SP-A, MMP-7, CCL-18, IL13, CC-chemokines, IL10, IL1 receptor antagonist, CCL2, Calgranulin B (S100A9 or MRP14), macrophage migration inhibitory factor (MIF), pro-collagen, or pro-collagen 3 or the presence and frequency of certain cell types in the body sample, such as fibrocytes and T-cell subpopulations.

The term "a body sample" as used herein means a sample obtained and isolated from a human subject. The body sample may be obtained by various known means, such as by biopsy tools, such as a needle biopsy tool or a bronchoscope, or by using a syringe.

In a further embodiment the body sample is selected from blood, serum, plasma, broncho-alveolar lavage fluid, and lung tissue.

As explained below several suitable test methods exists and such test methods are typically selected from an immunoassay, an immunohistochemical assay, a colorimetric assay, a turbidimetric assay, and flow cytometry.

In a further aspect the present invention relates to a method for treatment of pulmonary fibrosis, such as Idiopathic pulmonary fibrosis in a human subject having a galectin-3 level indicative of pulmonary fibrosis or exacerbation of symptoms comprising administering to a human subject a therapeutically effective amount of a galectin-3 inhibitor. In a particular embodiment the galectin-3 inhibitor is selected from the compound of formula (I).

In an embodiment the indicative level of galectin-3 is at least about 22 ng/ml, such as at least about 25 ng/ml, such as at least about 30 ng/ml, at least about 40 ng/ml, at least about 50 ng/ml, at least about 60 ng/ml, at least about 70 ng/ml.

In a further embodiment an additional step of monitoring the subject's galectin-3 blood level after the therapy is initiated. In particular, such monitoring is made in accordance with the invention as described herein.

The present invention provides methods for identification and evaluation of patients with pulmonary fibrosis by measuring the levels of markers such as galectin-3, optionally in combination with one or more other markers. Many methods for detecting of a protein of interest, with or without quantitation, are well known and can be used in the practice of the present invention. Such test methods are termed "a suitable test method" herein and several useful methods of testing are described below.

Examples of such assays are described below and can include, for example, immunoassays, chromatographic methods, and mass spectroscopy. Such assays can be performed on any biological sample including, among others, blood, plasma, and serum. Accordingly, multiple assays can be used to detect galectin-3, and samples can be analyzed from one or more sources.

Markers can be detected or quantified in a sample with the help of one or more separation methods. For example, suitable separation methods may include a mass spectrometry method, such as electrospray ionization mass spectrometry (ESI-MS), ESI-MS/MS, ESI-MS/(MS)n (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS) or atmospheric pressure photoionization mass spectrometry (APPI-MS), APPI-MS/MS, and APPI-(MS) Other mass spectrometry methods may include, inter alia, quadrupole, fourier transform mass spectrometry (FTMS) and ion trap. Spectrometric techniques that can also be used include resonance spectroscopy and optical spectroscopy.

Other suitable separation methods include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE), or other chromatographic techniques, such as thin-layer, gas or liquid chromatography, or any combination thereof. In one embodiment, the biological sample to be assayed may be fractionated prior to application of the separation method.

Markers can may be detected or quantified by methods that do not require physical separation of the markers themselves. For example, nuclear magnetic resonance (NMR) spectroscopy may be used to resolve a profile of a marker from a complex mixture of molecules.

A marker in a sample also may be detected or quantified, for example, by combining the marker with a binding moiety capable of specifically binding the marker. The binding moiety may include, for example, a member of a ligand-receptor pair, i.e., a pair of molecules capable of having a specific binding interaction. The binding moiety may also include, for example, a member of a specific binding pair, such as antibody-antigen, enzyme-substrate, nucleic acid-nucleic acid, protein-nucleic acid, protein-protein, or other specific binding pairs known in the art. Binding proteins may be designed which have enhanced affinity for a target. Optionally, the binding moiety may be linked with a detectable label, such as an enzymatic, fluorescent, radioactive, phosphorescent or colored particle label. The labeled complex may be detected, e.g., visually or with the aid of a spectrophotometer or other detector, or may be quantified.

Galectin-3 levels can be quantitated by performing an immunoassay. A galectin-3 immunoassay involves contacting a sample from a subject to be tested with an appropriate antibody under conditions such that immunospecific binding can occur if galectin-3 is present, and detecting or measuring the amount of any immunospecific binding by the antibody. Any suitable immunoassay can be used, including, without limitation, competitive and non-competitive assay systems using techniques such as Western blots, radioimmunoassays, immunohistochemistry, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays and protein A immunoassays.

In a "sandwich" assay, two molecules ("binding moieties") such as monoclonal antibodies that specifically bind to non-overlapping sites (epitopes) on galectin-3 are used. Typically, one binding moiety is immobilized on a solid surface where it binds with and captures galectin-3. This first binding moiety is therefore also referred to as the capture binding moiety. A second binding moiety is detectably labeled, for example, with a fluorophore, enzyme, or colored particle, such that binding of the second binding moiety to the galectin-3-complex indicates that galectin-3 has been captured. The intensity of the signal is proportional to the concentration of galectin-3 in the sample. The second binding moiety is therefore also referred to as the detection binding moiety or label binding moiety. A binding moiety can be any type of molecule, as long as it specifically binds to a portion of the N-terminus of galectin-3. In a preferred embodiment, the binding moieties used are monoclonal anti-galectin-3 antibodies, i.e., monoclonals raised against or otherwise selected to bind to separate portions of galectin-3.

Such assay procedures can be referred to as two-site immunometric assay methods, "sandwich" methods or (when antibodies are the binders) "sandwich immunoassays." As is known in the art, the capture and detection antibodies can be contacted with the test sample simultaneously or sequentially. Sequential methods can be accomplished by incubating the capture antibody with the sample, and adding the labeled detection antibody at a predetermined time thereafter (sometimes referred to as the "forward" method). Alternatively, the labeled detection antibody can be incubated with the sample first and then the sample can be exposed to the capture antibody (sometimes referred to as the "reverse" method). After any necessary incubation(s), which may be of short duration, to complete the assay, the label is measured. Such assays may be implemented in many specific formats known to those of skill in the art, including through use of various high throughput clinical laboratory analyzers or with a point of care or home testing device.

In one embodiment, a lateral flow device may be used in the sandwich format wherein the presence of galectin-3 above a baseline sensitivity level in a biological sample will permit formation of a sandwich interaction upstream of or at the capture zone in the lateral flow assay. See, for example, U.S. Pat. No. 6,485,982. The capture zone may contain capture binding moieties such as antibody molecules, suitable for capturing galectin-3, or immobilized avidin or the like for capture of a biotinylated complex. See, for example, U.S. Pat. No. 6,319,676. The device may also incorporate a luminescent label suitable for capture in the capture zone, the concentration of galectin-3 being proportional to the intensity of the signal at the capture site. Suitable labels include fluorescent labels immobilized on polystyrene microspheres. Colored particles also may be used.

Other assay formats that may be used in the methods of the invention include, but are not limited to, flow-through devices. See, for example, U.S. Pat. No. 4,632,901. In a flow-through assay, one binding moiety (for example, an antibody) is immobilized to a defined area on a membrane surface. This membrane is then overlaid on an absorbent layer that acts as a reservoir to pump sample volume through the device. Following immobilization, the remaining protein-binding sites on the membrane are blocked to minimize non-specific interactions. In operation, a biological sample is added to the membrane and filters through the matrix, allowing any analyte specific to the antibody in the sample to bind to the immobilized antibody. In a second step, a labeled secondary antibody may be added or released that reacts with captured marker to complete the sandwich. Alternatively, the secondary antibody can be mixed with the sample and added in a single step. If galectin-3 is present, a colored spot develops on the surface of the membrane.

The most common enzyme immunoassay is the "Enzyme-Linked Immunosorbent Assay (ELISA)." ELISA is a technique for detecting and measuring the concentration of an antigen using a labeled (e.g., enzyme-linked) form of the antibody. There are different forms of ELISA, which are well known to those skilled in the art. Standard ELISA techniques are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984), J. Clin. Chem. Clin. Biochem. 22:895-904. A preferred enzyme-linked immunosorbent assay kit (ELISA) for detecting galectin-3 is commercially available (BG Medicine, Waltham, Mass.).

In a "sandwich ELISA," an antibody (e.g., anti-galectin-3) is linked to a solid phase (i.e., a microtiter plate) and exposed to a biological sample containing antigen (e.g., galectin-3). The solid phase is then washed to remove unbound antigen. A labeled antibody (e.g., enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and .beta.-galactosidase. The enzyme linked antibody reacts with a substrate to generate a colored reaction product that can be measured. Any of the immunoassays described herein suitable for use with the kits and methods of the present invention can also use any binding moiety in the place of an antibody.

A detailed review of immunological assay design, theory and protocols can be found in numerous texts in the art, including Butt, W. R., Practical Immunology, ed. Marcel Dekker, New York (1984) and Harlow et al. Antibodies, A Laboratory Approach, ed. Cold Spring Harbor Laboratory (1988).

In general, immunoassay design considerations include preparation of antibodies (e.g., monoclonal or polyclonal antibodies) having sufficiently high binding specificity for the target to form a complex that can be distinguished reliably from products of nonspecific interactions. As used herein, the term "antibody" is understood to mean binding proteins, for example, antibodies or other proteins comprising an immunoglobulin variable region-like binding domain, having the appropriate binding affinities and specificities for the target. The higher the antibody binding specificity, the lower the target concentration that can be detected. As used herein, the terms "specific binding" or "binding specifically" are understood to mean that the binding moiety, for example, a binding protein, has a binding affinity for the target of greater than about $10^5 M^{-1}$, more preferably greater than about $10^7 M^{-1}$.

Antibodies to an isolated target marker which are useful in assays for detecting heart failure in an individual may be generated using standard immunological procedures well known and described in the art. See, for example Practical Immunology, supra. Briefly, an isolated marker is used to raise antibodies in a xenogeneic host, such as a mouse, goat or other suitable mammal. The marker is combined with a suitable adjuvant capable of enhancing antibody production in the host, and is injected into the host, for example, by intraperitoneal administration. Any adjuvant suitable for stimulating the host's immune response may be used. A commonly used adjuvant is Freund's complete adjuvant (an emulsion comprising killed and dried microbial cells and available from, for example, Calbiochem Corp., San Diego, or Gibco, Grand Island, N.Y.). Where multiple antigen injections are desired, the subsequent injections may comprise the antigen in combination with an incomplete adjuvant (e.g., cell-free emulsion). Polyclonal antibodies may be isolated from the antibody-producing host by extracting serum containing antibodies to the protein of interest. Monoclonal antibodies may be produced by isolating host cells that produce the desired antibody, fusing these cells with myeloma cells using standard procedures known in the immunology art, and screening for hybrid cells (hybridomas) that react specifically with the target and have the desired binding affinity.

Exemplary epitopes from the N-terminus of galectin-3 include, but are not limited to, MADNFSLHDALS (SEQ ID NO:1); MADNFSLHDALSGS (SEQ ID NO:2); WGNQPAGAGG (SEQ ID NO:3); YPGAPGAYPGAPAPGV (SEQ ID NO:4); GNPNPQGWPGA (SEQ ID NO:5); YPSSGQPSATGA (SEQ ID NO:6); YPGQAPPGAYPGQAPPGA (SEQ ID NO:7); YPGAPAPGVYPGPPSGPGA (SEQ ID NO:8); and YPSSGQPSATGA (SEQ ID NO:9). Other galectin-3 epitopes, including non-linear epitopes, can also be used as targets for detection by an anti-galectin-3 antibody. Exemplary antibodies are discussed in U.S. Patent Publication No. 2010/014954, the entire contents of which are incorporated herein by reference.

Antibody binding domains also may be produced biosynthetically and the amino acid sequence of the binding domain manipulated to enhance binding affinity with a preferred epitope on the target. Specific antibody methodologies are well understood and described in the literature. A more detailed description of their preparation can be found, for example, in Practical Immunology, (supra).

In addition, genetically engineered biosynthetic antibody binding sites, also known in the art as BABS or sFv's, may be used to determine if a sample contains a marker. Methods for making and using BABS comprising (i) non-covalently associated or disulfide bonded synthetic $V_H$ and $V_L$ dimers, (ii) covalently linked $V_H$-$V_L$ single chain binding sites, (iii) individual $V_H$ or $V_L$ domains, or (iv) single chain antibody binding sites are disclosed, for example, in U.S. Pat. Nos. 5,091,513; 5,132,405; 4,704,692; and 4,946,778. Furthermore, BABS having requisite specificity for the marker can be derived by phage antibody cloning from combinatorial gene libraries (see, for example, Clackson et al. Nature 352: 624-628 (1991)). Briefly, phages, each expressing on their coat surfaces BABS having immunoglobulin variable regions encoded by variable region gene sequences derived from mice pre-immunized with an isolated marker, or a fragment thereof, are screened for binding activity against the immobilized marker. Phages which bind to the immobilized marker are harvested and the gene encoding the BABS is sequenced. The resulting nucleic acid sequences encoding the BABS of interest then may be expressed in conventional expression systems to produce the BABS protein.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

EXPERIMENTAL

Synthesis of bis(3-deoxy-3-(3-fluorophenyl-1H-1,2,3-triazol-1-yl)-β-D-galactopyranosyl) sulfane General Methods.

Melting points were recorded on a Kofler apparatus (Reichert) and are uncorrected. Proton nuclear magnetic resonance (1H) spectra were recorded on a Bruker DRX 400 (400 MHz) or a Bruker ARX 300 (300 MHz) spectrometer;

multiplicities are quoted as singlet (s), doublet (d), doublet of doublets (dd), triplet (t), apparent triplet (at) or apparent triplet of doublets (atd). Carbon nuclear magnetic resonance (13C) spectra were recorded on a Bruker DRX 400 (100.6 MHz) spectrometer. Spectra were assigned using COSY, HMQC and DEPT experiments. All chemical shifts are quoted on the d-scale in parts per million (ppm). Low- and high-resolution (FAB-HRMS) fast atom bombardment mass spectra were recorded using a JEOL SX-120 instrument and low- and high-resolution (ES-HRMS) were recorded on a Micromass Q-TOF instrument. Optical rotations were measured on a Perkin-Elmer 341 polarimeter with a path length of 1 dm; concentrations are given in g per 100 mL. Thin layer chromatography (TLC) was carried out on Merck Kieselgel sheets, pre-coated with 60F254 silica. Plates were developed using 10% sulfuric acid. Flash column chromatography was carried out on silica (Matrex, 60 Å, 35-70 μm, Grace Amicon). Acetonitrile was distilled from calcium hydride and stored over 4 Å molecular sieves. DMF was distilled from 4 Å molecular sieves and stored over 4 Å molecular sieves.

Bis(3-deoxy-3-(3-fluorophenyl-1H-1,2,3-triazol-1-yl)-β-D-galactopyranosyl) sulfane (TD139) was prepared in accordance with the reaction scheme 1 below:

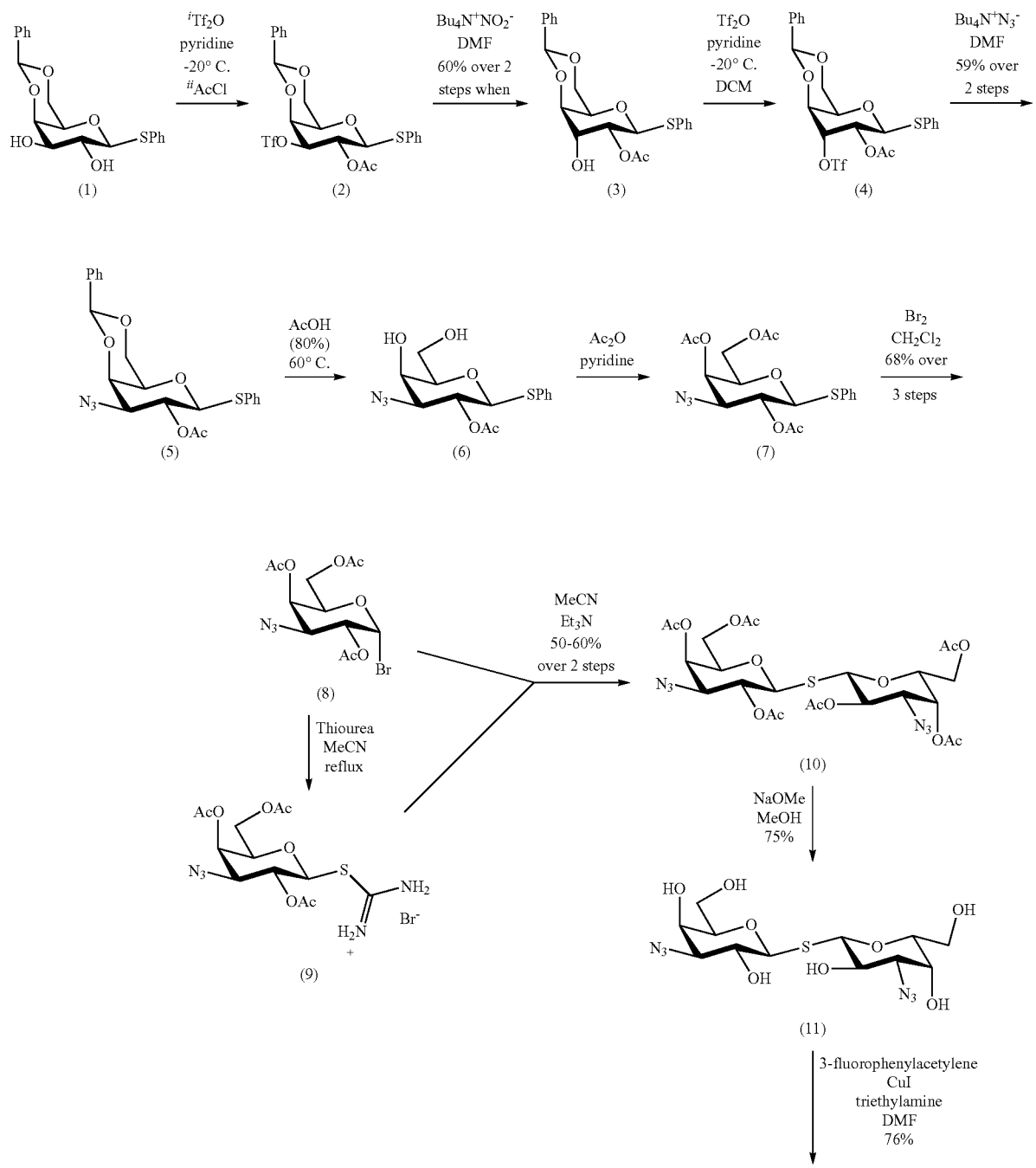

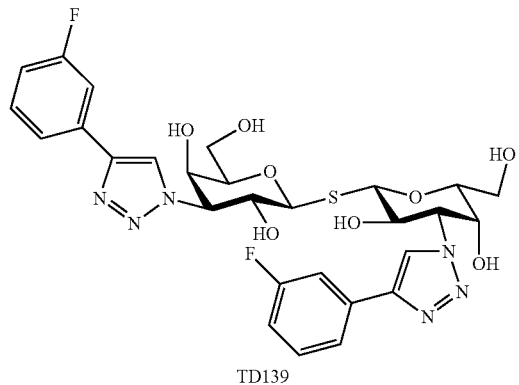

TD139

Compound (1) (cf. reaction scheme above) is commercial from Carbosynth Limited 8 & 9 Old Station Business Park-Compton-Berkshire-RG20 6NE-UK or synthesized in three near-quantitative steps from D-galactose, (cf e.g. Li, Z. and Gildersleeve, J. C. J. Am. Chem. Soc. 2006, 128, 11612-11619)

Phenyl 2-O-acetyl-4,6-O-benzylidene-1-thio-3-O-trifluoromethanesulfonyl-β-D-galactopyranoside (2)

Compound 1 (10.5 g, 29.2 mmol) was dissolved in dried pyridine (4.73 mL, 58.4 mmol) and dried CH$_2$Cl$_2$ (132 mL). The reaction mixture was cooled, under stirring, until −20° C. (Ice and NaCl bath 3:1). Slowly and under N$_2$ atmosphere, Tf$_2$O (5.68 mL, 33.6 mmol) was added. The reaction mixture was monitored by TLC (heptane:EtOAc, 1:1 and toluene:acetone, 10:1). When the reaction was complete, AcCl (2.29 mL, 32.1 mmol) was added and keeping stirring, the temperature was increased to room temperature. This mixture was monitored by TLC too (heptane:EtOAc, 1:1 and toluene:acetone, 10:1). When it was complete, it was quenched with CH$_2$Cl$_2$ and washed with 5% HCl, NaHCO$_3$ (saturated—hereafter sat) and NaCl (sat). The organic layer was dried over MgSO$_4$, filtered and concentrated under reduced pressure.

Phenyl 2-O-acetyl-4,6-O-benzyliden-1-thio-β-D-gulopyranoside (3)

Tetrabutylammonium nitrite (25.3 g, 87.7 mmol) was added to a solution of compound 2 (15.6 g, 29.2 mmol) in DMF (110 mL) and was kept stirring, under N$_2$ atmosphere, at 50° C. (The reaction started being purple and turned garnet). The reaction was monitored by TLC (heptane:EtOAc, 1:1 and toluene:acetone, 10:1) and quenched with CH$_2$Cl$_2$. The mixture was washed with 5% HCl, NaHCO$_3$ (sat) and NaCl (sat). The organic layer was dried over MgSO$_4$, filtered and concentrated under reduced pressure followed by purification by flash chromatography (Eluent heptane:EtOAc, 1:1 and heptane:EtOAc, 1:2) and recrystallized from a mixture of EtOAc and Heptane (1:3). $^1$H NMR in CDCl$_3$ δ 7.60-7.57 (m, 2H, Ar), 7.43-7.40 (m, 2H, Ar), 7.37-7.34 (m, 3H, Ar), 7.29-7.25 (m, 3H, Ar), 5.50 (s, 1H, PhCH), 5.15 (d, 1H, J=10.29 Hz, H-1), 5.10 (dd, 1H, J=10.27 Hz, 2.85 Hz, H-2), 4.36 (dd, 1H, J=12.49 Hz, 1.4 Hz, H-6), 4.18 (br s, 1H, H-3), 4.08 (dd, 1H, J=3.59 Hz, 1.04 Hz, H-6), 4.03 (dd, 1H, J=12.53 Hz, 1.75 Hz, H-4), 3.88 (s, 2H, H-5+OH), 2.12 (s, 3H, OAc).

Phenyl 2-O-acetyl-4,6-O-benzylidene-1-thio-3-O-trifluoromethanesulfonyl-β-D-gulopyranoside (4)

Compound 3 (1.00 g, 2.48 mmol) was dissolved in dried CH$_2$Cl$_2$ (12.5 mL) and dried pyridine (0.40 mL, 4.96 mmol). The reaction mixture was cooled, under stirring, until −20° C. (Ice and NaCl bath 3:1). Slowly and under N$_2$ atmosphere, Tf$_2$O (0.48 mL, 2.85 mmol) was added. The reaction mixture was monitored by TLC (heptane:EtOAc, 1:1 and toluene:acetone, 10:1) and when it was complete, it was quenched with CH$_2$Cl$_2$ and washed with 5% HCl, NaHCO$_3$ (sat) and NaCl (sat). The organic layer was dried over MgSO$_4$, filtered and concentrated under reduced pressure until being dry.

Phenyl 2-O-acetyl-3-azido-4,6-O-benzylidene-3-deoxy-1-thio-β-D-galactopyranoside (5)

Tetrabutylammonium azide (2.12 g, 7.44 mmol) was added carefully to a solution of compound 4 (1.3256 g, 2.48 mmol) in DMF (10 mL) and was kept stirring, under N$_2$ atmosphere, at 50° C. The reaction was monitored by TLC (E:H, 1:1) and concentrated under reduced pressure followed by purification by flash chromatography (Eluent heptane:EtOAc, 2:1 and heptane:EtOAc, 1:1). $^1$H NMR in CDCl$_3$ δ 7.61-7.58 (m, 2H, Ar), 7.44-7.41 (m, 2H, Ar), 7.39-7.36 (m, 3H, Ar), 7.30-7.24 (m, 3H, Ar), 5.59 (s, 1H, PhCH), 5.35 (t, 1H, J=9.95 Hz, H-2), 4.73 (d, 1H, J=9.63 Hz, H-1), 4.44 (dd, 1H, J=6.24 Hz, 1.60 Hz, H-6), 4.35-4.34 (dd, 1H, J=3.33 Hz, 0.88 Hz, H-4), 4.11 (dd, 1H, J=12.48 Hz, 1.67 Hz, H-6), 3.57 (d, 1H, J=1.15 Hz, H-5), 3.44 (dd, 1H, J=10.21 Hz, 3.29 Hz, H-3), 2.17 (s, 3H, OAc).

Phenyl 2-O-acetyl-3-azido-3-deoxy-1-thio-β-D-galactopyranoside (6)

Compound 5 (470 mg, 1.1 mmol) was dissolved in 80% acetic acid (75 mL) and the mixture was heated at 60° C. The reaction was monitored by TLC (heptane:EtOAc, 1:1). When the reaction was complete, the mixture was concentrated under reduced pressure and heating.

Phenyl 2,4,6-tri-O-acetyl-3-azido-3-deoxy-1-thio-β-D-galactopyranoside (7)

Acetic anhydride (30 mL) was added to a solution of compound 6 (373 mg, 1.1 mmol) in dry pyridine (30 mL). The reaction was monitored by TLC (heptane:EtOAc, 1:1) and when it was complete, it was concentrated under reduced pressure. $^1$H NMR in CDCl$_3$ δ 7.54-7.51 (m, 2H, Ar), 7.35-7.30 (m, 3H, Ar), 5.46 (dd, 1H, H-4), 5.23 (t, 1H, H-2), 4.73 (d, 1H, H-1), 4.15 (d, 2H, H-6, H-6), 3.94 (dt, 1H, H-5), 3.68 (dd, 1H, H-3), 2.18 (s, 3H, OAc), 2.15 (s, 3H, OAc), 2.06 (s, 3H, OAc).

2,4,6-tri-O-acetyl-3-azido-3-deoxy-α-D-galactopyranosyl bromide (8)

Compound 7 (237.4 mg, 560 μmol) was dissolved in dry CH$_2$Cl$_2$ (2 mL), and bromine (32 μl, 620 μmol) was added. The reaction was monitored by TLC (heptane:EtOAc, 1:1). When the reaction was complete, a small amount of cyclopentene was added to the reaction mixture to remove the rests of Br$_2$. The mixture was concentrated under reduced pressure and purified by quick Flash chromatography (Eluent: 500 mL heptane:EtOAc, 2:1).

2,4,6-tri-O-acetyl-3-azido-3-deoxy-α-D-galactopyranose-1-isothiouronium bromide (9)

The sensitive bromide 8 (70.6 mg, 180 μmol) was immediately dissolved in dry acetonitrile (1.7 mL) and refluxed with thiourea (13.7 mg, 180 μmol) under N$_2$ for 4 hours. The reaction was monitored by TLC (heptane:EtOAc, 1:1) and when it was complete, the mixture was cooled.

Bis-(2,4,6-tri-O-acetyl-3-azido-3-deoxy-b-D-galactopyranosyl)-sulfane (10)

The sensitive bromide 8 (77.0 mg, 196 μmol) and Et$_3$N (60 μl, 430 μmol) was added to the last mixture (9). The reaction was monitored by TLC (heptane:EtOAc, 1:1). When it was complete, the reaction mixture was concentrated under reduced pressure and without heating. The residue was purified by flash chromatography (Eluent: heptane:EtOAc, 1:1). $^1$H NMR in CDCl$_3$ δ 5.50 (dd, 2H, H-4,), 5.23 (t, 2H, H-2, H-2'), 4.83 (d, 2H, H-1, H-1'), 4.15 (dd, 4H, H-6, H-6, H-6', H-6'), 3.89 (dt, 2H, H-5, H-5'), 3.70 (dd, 2H, H-3, H-3'), 2.19 (s, 6H, 2OAc), 2.15 (s, 6H, 2OAc), 2.18 (s, 6H, 2OAc).

Bis-(3-azido-3-deoxy-β-D-galactopyranosyl)-sulfane (11)

Compound 10 (160 mg, 0.00024 mol) was dissolved in dry MeOH (2.6 mL) and dry CH$_2$Cl$_2$ (1.6 mL), and NaOMe (1M, 24 μL, 24 μmol) was added. The reaction was monitored by TLC (heptane:EtOAc 1:1 and D:M 5:1). When the reaction was complete, the mixture was neutralized with Duolite C436 until pH 7, filtered and washed with MeOH. The filtered solution was concentrated under reduced pressure. The residue was purified by flash chromatography (Eluent: CH$_2$Cl$_2$:MeOH, 5:1) to give pure 11 (74.1 mg, 75%). 1H NMR in CDCl$_3$ δ 4.72 (d, 2H, J=9.7 Hz, H-1, H-1'), 3.95 (br s, 2H, H-4, H-4'), 3.84 (t, 2H, J=9.8 Hz, H-2, H-2'), 3.74 (dd, 2H, J=11.47 Hz, 7.23 Hz, H-6, H-6'), 3.64 (dd, 2H, J=11.48 Hz, 4.72 Hz, H-6, H-6'), 3.60-3.55 (ddd, 2H, 7.15 Hz, 4.67 Hz, 0.93 Hz, H-5, H-5'), 3.36 (dd, 2H, J=10 Hz, 3.05 Hz, H-3, H-3').

Bis-{3-deoxy-3-[4-(3-fluorophenyl)-1H-1,2,3-triazol-1-yl]-β-D-galactopyranosyl}sulfane (Named TD139)

TD139 was synthesized at ambient temperature by Cu(I)-catalyzed cycloaddition between bis-(3-azido-3-deoxy-β-D-galactopyranosyl)-sulfane (11) and 3-fluorophenylacetylene (3 eq.) with Cu(I) (0.2 eq), triethylamine (2 eq.) in N,N-dimethylformamide (DMF, 100 mL/mmol sulfane). The reaction was monitored with tlc until complete, concentrated and first purified by flash chromatography (Eluent: CH$_2$Cl$_2$:MeOH, 8:1), followed by final purification by preparative hplc to give TD139 in 76% yield as a white amorphous solid. $^1$H-NMR (CD$_3$OD, 400 MHz) d 8.59 (s, 2H, triazole-H), 7.63 (br d, 2H, 7.6 Hz, Ar—H), 7.57 (br d, 2H, 8.4 Hz, Ar—H), 7.41 (dt, 2H, 6.0 and 8.0 Hz, Ar—H), 7.05 (br dt, 2H, 2.4 and 6.4 Hz, Ar—H), 4.93 (dd, 2H, 2.4 and 10.4 Hz, H3), 4.92 (d, 2H, 10.4 Hz, H1), 4.84 (2H, 10.4 Hz, H2), 4.18 (d, 2H, 2.4 Hz, H4), 3.92 (dd, 2H, 4.2 and 7.6 Hz, H5), 3.84 (dd, 2H, 7.6 and 11.4 Hz, H6), 3.73 (dd, 2H, 4.2 and 11.4 Hz, H6); FAB-HRMS m/z calcd for C$_{28}$H$_{30}$F$_2$N$_6$NaO$_8$S (M+Na$^+$), 671.1712. found, 671.1705.

Model of Bleomycin-Induced Lung Fibrosis

Female C57/Bl6 mice (10-14 weeks old) were anaesthetized with halothane, and bleomycin or saline was administered intratracheally (33 μg in 50 μl of saline) and lungs were harvested on day 26. TD139 was instilled into the lungs of mice on days 18, 20, 22 and 24 of bleomycin induced lung injury. Fibrosis was assessed by histological score of collagen stained lung sections and by total collagen content by Sircol assay.

Mice were treated with bleomycin (bleo) or saline (control) and bleomycin treated mice were treated with 200 mg/kg pirfenidone twice daily on days 18-24. TD139 was administered intratracheally on days 18, 20, 22 and 24. Lungs were harvested on day 26. Results are shown in FIG. 1.

Effect on Alveolar Epithelial Cells

Primary alveolar epithelial cells from WT mice were plated and treated with TGF-β1 in the presence or absence of 10 μM TD139. FIG. 1D) Cells were lysed and analyzed for active β-catenin, total β-catenin and β-actin by western blot. In conclusion TD139 is a galectin-3 inhibitor and blocked TGF-β-induced β-catenin activation in vitro and bleomycin induced lung fibrosis in vivo and is believed to represent a novel therapeutic strategy for treatment of lung fibrosis in mammals, in particular humans.

Drug Treatment

Mice were divided into the following groups set forth in Table I:

Immunohistochemistry

Paraffin-embedded sections of mouse tissue were stained with Masson's trichrome and haemotoxylin and eosin (H&E) as per manufacturer's instructions. Sections were processed for immunohistochemistry and the following primary antibodies used: mouse anti-active (ABC) beta-catenin (Millipore) and sections visualized and quantified.

TABLE I

| Group | Induction | Treatment | Dose | Dosing days | Administration |
|---|---|---|---|---|---|
| 1 | Control | Vehicle | | N/A | |
| 2 | Bleomycin | Vehicle | | 18, 20, 22 and 24 | Intratracheal |
| 3 | Bleomycin | TD139 | 10 ug | 18, 20, 22 and 24 | Intratracheal |
| 4 | Bleomycin | TD139 | 3 ug | 18, 20, 22 and 24 | Intratracheal |
| 5 | Bleomycin | TD139 | 1 ug | 18, 20, 22 and 24 | Intratracheal |
| 6 | Bleomycin | TD139 | 0.1 ug | 18, 20, 22 and 24 | Intratracheal |

TABLE I-continued

| Group | Induction | Treatment | Dose | Dosing days | Administration |
|---|---|---|---|---|---|
| 7 | Bleomycin | Pirfenidone | 200 mg/kg | b.i.d. from day 18 | oral |

Determination of Lung Fibrosis and Inflammation

Histological lung inflammation and fibrosis score were carried out in Masson's trichrome stained sections. Inflammation (peribronchiolar, perivascular, and alveolar wall thickness) scored in >5 random fields at magnification X630 using the following system (peribronchiolar and perivascular, 1=no cells, 2=<20 cells, 3=20-100 cells, 4=>100 cells; alveolar wall thickness, 1=no cells, 2=2-3 cells thick, 3=4-5 cells thick, 4=>5 cells thick). The combined inflammatory score was the sum of these scores. Fibrosis score was evaluated as the area of the section positively stained for collagen (1=none, 2=<10%, 3=<50%, 4=>50%). Only fields where the majority of the field was composed of alveoli were scored.

Determination of Lung Collagen by Sircol Assay

Collagen content in the left lung lobe was determined by sircol assay as per manufacturer's instructions. The left lobe was minced in 5 ml of 3 mg/ml pepsin in 0.5 M acetic acid and incubated with shaking at 4° C. for 24 h. Cleared lung extract (0.2 ml) was incubated with 0.8 ml sircol reagent for 1 h at room temperature and precipitated collagen centrifuged at 10,000 g for 5 min at 4° C. Pellets solubilised in 1 ml 1 M NaOH and absorbance measured at 570 nm alongside collagen standards.

Primary Type II Alveolar Epithelial Cell Isolation

Treated and control mouse type II lung alveolar epithelial cells (AECs) were extracted following a standard method. Briefly, 1 ml of 50 U/ml dispase (BD Biosciences) was administered intratracheally into perfused lungs followed by instillation of 0.5 ml of 1% low melting point agarose. The agarose within the upper airways was allowed to set on ice for 2 minutes and the lungs were placed in 4 ml 50 U/ml dispase for 45 min at room temperature. The lung lobes minus the upper airways were then dispersed in DMEM containing 50 µg/ml DNAse I (Sigma-Aldrich, UK). The cell suspension was passed through a 100-µm cell strainer and the cells washed in DMEM followed by resuspension in DMEM containing 10% FCS. The cell suspension was plated onto tissue culture plastic for 1 h to allow any contaminated fibroblasts and macrophages to adhere. Non-adherent epithelial cells were counted and cultured for 2 days on tissue culture plastic or cover-slips pre-coated with 5 µg/ml collagen (AMS Biotechnology) and 10 µg/ml fibronectin (Sigma-Aldrich), Cells were washed three times in PBS before treatment. Epithelial cells were either incubated in DMEM containing 10% FCS, 50 U/ml penicillin, 50 µg/ml streptomycin and 5 µg/ml L-glutamine or transferred to complete mouse media (DMEM/F-12 containing 0.25% BSA, 10 nM hydrocortisone, 5 µg/ml Insulin-Transferrin-Sodium-Selenite (ITS) and supplemented with 0.1 mg/ml sodium succinate, 75 µg/ml succinic acid and 1.8 µg/ml choline bitartrate).

Western Blotting

Cells were lysed in 25 mM HEPES pH 7.4, 0.3 M NaCl, 1.5 mM MgCl2, 0.2 mM EDTA, 0.5% triton X-100, 0.5 mM dithiothreitol, 1 mM sodium orthovanadate and protease inhibitors (Boehringer Mannheim, Sussex, UK; prepared as per manufacturers instructions). Lysates equilibrated for protein using Pierce BCA protein assay reagent (Pierce) and resolved on 12% SDS-PAGE gels. Western blot analysis undertaken using the following primary antibodies; rabbit anti beta-catenin, (BD Biosciences), rabbit polyclonal anti-beta-actin antibody (Sigma, UK), mouse anti-active (ABC) beta-catenin (Millipore).

Example 1

Measurement of Galectin-3 Levels in Human Lung Biopsies

Biopsies were sampled from patients with usual interstitial pneumonia (UIP), the most common cause of IPF. Biopsies were fixed in neutral buffered formalin for 12-24 h prior to embedding in paraffin wax for sectioning. 5 um sections were cut and transferred onto glass slides. Sections were dewaxed in xylene for 10 mins and rehydrated by placing slides for 2 min each in graded ethanol (100%-95%-80%-70%-50%-water) Antigen retrieval was performed by microwaving sections in 0.01M citrate pH 6.0 for 15 min. After cooling in running tap water peroxidase was blocked by incubating in 1% hydrogen peroxide solution for 15 mins. Slides were rinsed in phosphate buffered saline (PBS) and non specific binding was blocked using serum free protein block and avidin/biotin blocking kit (Vector Laboratories, USA). The sections were incubated with mouse monoclonal anti-human galectin-3 clone 9C4 from Novocastra. (diluted to 1:100 in antibody diluent, DAKO, UK) overnight at 4° C. After 3 washes with PBS, sections were incubated with biotinylated rabbit anti-mouse IgG (H+L) secondary antibody (diluted 1:200 in antibody diluent) for 30 minutes at room temperature. Slides were rinsed 3 times with PBS and incubated with 3 drops of avidin:biotinylated enzyme complex (R.T.U. Vectastain Elite ABC Reagent, PK-7100, Vector Labs, Burlingame, Calif., USA) for 30 minutes followed by liquid diaminobenzidine (DAB) (Liquid DAB+Substrate Chromogen System, K3468, Dako UK Ltd, Cambridgeshire) in the dark for 10 minutes.

Slides were rinsed 3 times in PBS, counterstained for 30 seconds with Mayers haematoxylin (ThermoShandon, UK) and 30 seconds in Scotts tap water (83 mM MgSO4, 7.1 mM NaHCO3 in tap water), dehydrated through graded ethanol (70%, 90%, 100% 2 min each), and cleared in xylene. Slides were mounted using Pertex mounting solution (CellPath Hemel Hempstead, UK).

Sections were visualized by light microscopy.

Galectin-3 is markedly up-regulated in fibroproliferative areas in the lung of patients with UIP.

Example 2

Method for Measurement of Galectin-3 Levels in Human Serum or Human Broncho-Alveolar Lavage Fluid 1. Dilute the Capture Antibody to the working concentration in PBS without carrier protein. Immediately coat a 96-well microplate6 with 100 µL per well of the diluted Capture Antibody. Seal the plate and incubate overnight at room temperature.

2. Aspirate each well and wash with Wash Buffer, repeating the process two times for a total of three washes. Wash by filling each well with Wash Buffer (400 µL) using a squirt bottle, manifold dispenser, or autowasher. Complete removal of liquid at each step is essential for good performance. After the last wash, remove any remaining Wash Buffer by aspirating or by inverting the plate and blotting it against clean paper towels.

3. Block plates by adding 300 µL of Reagent Diluent to each well. Incubate at room temperature for a minimum of 1 hour.

4. Repeat the aspiration/wash as in step 2. The plates are now ready for sample addition.

Assay Procedure

1. Add 100 µL of sample or standards in Reagent Diluent, or an appropriate diluent, per well. Cover with an adhesive strip and incubate 2 hours at room temperature.

2. Repeat the aspiration/wash as in step 2 of Plate Preparation.

3. Add 100 µL of the Detection Antibody, diluted in Reagent Diluent, to each well. Cover with a new adhesive strip and incubate 2 hours at room temperature.

4. Repeat the aspiration/wash as in step 2 of Plate Preparation.

5. Add 100 µL of the working dilution of Streptavidin-HRP to each well. Cover the plate and incubate for 20 minutes at room temperature. Avoid placing the plate in direct light.

6. Repeat the aspiration/wash as in step 2.

7. Add 100 µL of Substrate Solution to each well. Incubate for 20 minutes at room temperature. Avoid placing the plate in direct light.

8. Add 50 µL of Stop Solution to each well. Gently tap the plate to ensure thorough mixing.

9. Determine the optical density of each well immediately, using a microplate reader set to 450 nm. If wavelength correction is available, set to 540 nm or 570 nm. If wavelength correction is not available, subtract readings at 540 nm or 570 nm from the readings at 450 nm. This subtraction will correct for optical imperfections in the plate. Readings made directly at 450 nm without correction may be higher and less accurate.

Example 3

Measurement of Galectin-3 Levels in Serum from Patients and Controls

Serum was sampled from patients with UIP, patients with non-specific interstitial pneumonia (NSIP) and aged matched controls. Galectin-3 levels were measured using the ELISA method described in example 2. Serum was collected and stored at −80° C. prior to assay. Samples were normally diluted 1:10 in PBS prior to assay. ELISA was carried out as described in the manufacturers protocol:

Galectin-3 was measured serially (on 2-5 occasions) in the serum of 6 patients with stable IPF (UIP). Stable IPF was defined as no significant change in exercise tolerance, breathlessness or lung function. Galectin-3 was elevated in the serum of patients with IPF (control $17.9 \pm 0.95$ ng/ml n=8, IPF $26.7 \pm 4.7$ ng/ml n=6, P<0.05) but not in patients with non-specific interstitial pneumonia (NSIP) (serum concentration $14.57 \pm 0.84$ ng/ml (n=10)).

The serum level of galectin-3 remains remarkably constant over time in these patients (serum galectin-3 $25.5 \pm 0.8$ ng/ml n=23). We tested 5 serum samples from patients undergoing an acute exacerbation of IPF. These patients were defined as having an acute exacerbation by decreased exercise to tolerance, decreased lung function and increased breathlessness. In these patients there was a dramatic rise in serum galectin-3, $73.8 \pm 12.2$ ng/ml. Furthermore, we identified 2 patients who had serial galectin-3 measurements prior and during an acute exacerbation of their IPF. Both patients show stable galectin-3 serum levels during the period while their lung function was stable. However, during an acute exacerbation when lung function declined there was a sharp rise in serum galectin-3.

Example 4

Measurement of Galectin-3 Levels in BAL Fluid from Patients and Controls

Broncho-alveolar lavage (BAL) fluid was sampled from IPF patients and age matched controls using a standard technique. Briefly, a bronchoscope was passed through the mouth or nose into the lungs and a small lung section was flushed with a specified amount of saline. The BAL fluid was collected and stored at −80° C. The level of Galectin-3 was measured using the ELISA method described in Example 2.

Galectin-3 levels were significantly elevated in BAL samples from IPF patients compared to age matched controls (control $18.8 \pm 3.6$ ng/ml n=16, IPF $39.7 \pm 3.7$ ng/ml n=15, P<0.01).

What is claimed is:

1. A compound of formula (I):

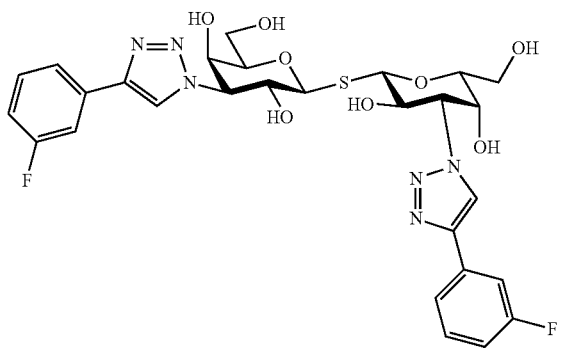

(I)

in amorphous form.

2. The compound of claim 1 wherein said compound is 3,3'-Dideoxy-3,3'-bis-[4-(3-fluorophenyl)-1H-1,2,3-triazol-1-yl]-1,1'-sulfanediyl-di-β-D-galactopyranoside in free form.

3. A composition comprising the compound of claim 1 and optionally a pharmaceutically acceptable additive.

4. A method for treatment of pulmonary fibrosis comprising administering to a mammal in need thereof an amount of the compound of claim 1 effective to treat said pulmonary fibrosis.

5. The method of claim 4, wherein said compound is administered by the pulmonary route.

6. A process of preparing the compound of claim 1, comprising a step of reacting bis-(3-deoxy-3-azido-β-D-galactopyranosyl) sulfane with 3-fluorophenylacetylene and an amine in a solvent, resulting in said compound which after purification and isolation provide the amorphous form of the compound of formula (I).

7. The process of claim 6, wherein the amine is triethylamine, a catalyst is present and is selected from Cu(I), and the solvent is an organic solvent selected from DMF.

* * * * *